US012622745B2

(12) United States Patent
Cohn et al.

(10) Patent No.: US 12,622,745 B2
(45) Date of Patent: May 12, 2026

(54) SYSTEMS AND METHODS FOR SEALING CORED OR PUNCTURED TISSUE USING INFLATABLE BALLOON

(71) Applicant: Prana Thoracic, Inc., Houston, TX (US)

(72) Inventors: William Cohn, Bellaire, TX (US); Terry Daglow, Houston, TX (US); Matthew Kuhn, Houston, TX (US); Steven Nguyen, Cypress, TX (US)

(73) Assignee: Prana Thoracic, Inc., Houston, TX (US)

( * ) Notice: Subject to any disclaimer, the term of this patent is extended or adjusted under 35 U.S.C. 154(b) by 0 days.

(21) Appl. No.: 17/201,166

(22) Filed: Mar. 15, 2021

(65) Prior Publication Data

US 2021/0338316 A1     Nov. 4, 2021

Related U.S. Application Data

(60) Provisional application No. 63/017,734, filed on Apr. 30, 2020.

(51) Int. Cl.
A61B 17/00 (2006.01)
A61B 18/00 (2006.01)
A61B 18/14 (2006.01)

(52) U.S. Cl.
CPC .. A61B 18/1477 (2013.01); A61B 2018/0022 (2013.01); A61B 2018/00541 (2013.01); A61B 2018/00577 (2013.01); A61B 2018/0063 (2013.01); A61B 2018/00714 (2013.01)

(58) Field of Classification Search
CPC .. A61B 2018/0022; A61B 2018/00214; A61B 2018/00226; A61B 2018/00232; A61B 2018/00238; A61B 2018/00244; A61B 2018/0025; A61B 2018/00255; A61B 2018/00261
See application file for complete search history.

(56) References Cited

U.S. PATENT DOCUMENTS

| | | | |
|---|---|---|---|
| 4,007,732 A | 2/1977 | Kvavle et al. |
| 4,735,194 A | 4/1988 | Stiegmann |
| 5,103,804 A | 4/1992 | Abele et al. |
| 5,133,360 A | 7/1992 | Spears |
| 5,190,561 A | 3/1993 | Graber |
| 5,196,024 A | 3/1993 | Barath |
| 5,353,804 A | 10/1994 | Kornberg et al. |
| (Continued) | | |

FOREIGN PATENT DOCUMENTS

| | | |
|---|---|---|
| CN | 1221603 A | 7/1999 |
| CN | 102656171 A | 9/2012 |
| (Continued) | | |

OTHER PUBLICATIONS

Bhamidipati et al., BioGlue in 2011: What is its Role in Cardiac Surgery, Mar. 2012 (Year: 2012).*

(Continued)

*Primary Examiner* — Linda C Dvorak
*Assistant Examiner* — Nicholas S Borsch

(57) ABSTRACT

Systems and methods for sealing tissue sites may comprise coring tissue at a target site such that a tissue core is removed from the target site thereby creating a core cavity at the target site and causing sealing of at least a portion of the target site.

27 Claims, 15 Drawing Sheets

(56)                    References Cited

U.S. PATENT DOCUMENTS

| | | | |
|---|---|---|---|
| 5,507,743 A | 4/1996 | Edwards et al. | |
| 5,643,282 A | 7/1997 | Kieturakis | |
| 5,651,788 A | 7/1997 | Fleischer et al. | |
| 5,681,281 A | 10/1997 | Vigil et al. | |
| 5,779,698 A | 7/1998 | Clayman et al. | |
| 5,810,811 A | 9/1998 | Yates et al. | |
| 5,843,108 A | 12/1998 | Samuels | |
| 5,882,316 A | 3/1999 | Chu et al. | |
| 5,908,435 A | 6/1999 | Samuels | |
| 5,928,163 A | 7/1999 | Roberts et al. | |
| 5,961,526 A | 10/1999 | Chu et al. | |
| 6,022,362 A | 2/2000 | Lee et al. | |
| 6,213,957 B1 | 4/2001 | Milliman et al. | |
| 6,258,108 B1 | 7/2001 | Lary | |
| 6,493,589 B1* | 12/2002 | Medhkour | A61N 1/3702 |
| | | | 606/41 |
| 6,574,513 B1 | 6/2003 | Collura et al. | |
| 6,652,520 B2 | 11/2003 | Moorman et al. | |
| 6,770,070 B1 | 8/2004 | Balbierz | |
| 6,974,467 B1 | 12/2005 | Gonzales, Jr. | |
| 7,517,352 B2 | 4/2009 | Evans et al. | |
| 7,582,055 B2 | 9/2009 | Komiya et al. | |
| 7,811,303 B2 | 10/2010 | Fallin et al. | |
| 8,239,030 B1 | 8/2012 | Hagedorn et al. | |
| 8,506,503 B2 | 8/2013 | Fritscher-Ravens et al. | |
| 8,602,973 B2 | 12/2013 | Wendlandt | |
| 8,734,362 B2* | 5/2014 | Boyle, Jr. | A61B 17/12104 |
| | | | 600/564 |
| 9,241,692 B2 | 1/2016 | Gunday et al. | |
| 9,521,961 B2 | 12/2016 | Silverstein et al. | |
| 9,895,190 B2 | 2/2018 | Trieu | |
| 10,022,179 B2 | 7/2018 | Feinberg et al. | |
| 10,039,529 B2 | 8/2018 | Kerr et al. | |
| 10,130,369 B2 | 11/2018 | Fung et al. | |
| 10,314,578 B2 | 6/2019 | Leimbach et al. | |
| 10,413,368 B2 | 9/2019 | Nilsagard et al. | |
| 10,555,769 B2 | 2/2020 | Worrell et al. | |
| 10,595,835 B2 | 3/2020 | Kerr et al. | |
| 11,103,272 B2 | 8/2021 | Boyle et al. | |
| 11,331,087 B2 | 5/2022 | Boyle, Jr. | |
| 11,723,708 B2 | 8/2023 | Cohn et al. | |
| 12,102,372 B2 | 10/2024 | Cohn et al. | |
| 2002/0019597 A1* | 2/2002 | Dubrul | A61B 10/0266 |
| | | | 600/567 |
| 2002/0049442 A1 | 4/2002 | Roberts et al. | |
| 2002/0059938 A1 | 5/2002 | Fogarty et al. | |
| 2002/0082614 A1 | 6/2002 | Logan et al. | |
| 2002/0095101 A1 | 7/2002 | Fontenot | |
| 2002/0095152 A1* | 7/2002 | Ciarrocca | A61B 18/1492 |
| | | | 606/50 |
| 2002/0115997 A1 | 8/2002 | Truckai et al. | |
| 2003/0114911 A1 | 6/2003 | Lupton | |
| 2003/0129382 A1 | 7/2003 | Treat | |
| 2003/0233099 A1 | 12/2003 | Danaek et al. | |
| 2004/0010206 A1 | 1/2004 | Dubrul et al. | |
| 2004/0122349 A1 | 6/2004 | Lafontaine et al. | |
| 2004/0133254 A1* | 7/2004 | Sterzer | A61B 18/18 |
| | | | 607/101 |
| 2004/0147917 A1 | 7/2004 | Mueller et al. | |
| 2004/0215296 A1* | 10/2004 | Ganz | A61B 5/0538 |
| | | | 607/101 |
| 2004/0254572 A1 | 12/2004 | McIntyre et al. | |
| 2005/0113854 A1 | 5/2005 | Uckele | |
| 2005/0288695 A1 | 12/2005 | Jenson et al. | |
| 2006/0009756 A1* | 1/2006 | Francischelli | A61B 18/14 |
| | | | 606/41 |
| 2006/0025815 A1 | 2/2006 | McGurk et al. | |
| 2006/0069388 A1 | 3/2006 | Truckai et al. | |
| 2006/0074484 A1 | 4/2006 | Huber | |
| 2006/0190037 A1 | 8/2006 | Ginn et al. | |
| 2007/0005084 A1 | 1/2007 | Clague et al. | |
| 2007/0015984 A1 | 1/2007 | Yeo et al. | |
| 2007/0043350 A1* | 2/2007 | Soltesz | A61B 18/20 |
| | | | 606/41 |

| | | | |
|---|---|---|---|
| 2007/0073343 A1 | 3/2007 | Jahns et al. | |
| 2007/0123852 A1* | 5/2007 | Deem | A61B 18/1492 |
| | | | 606/45 |
| 2007/0156156 A1 | 7/2007 | Badie | |
| 2007/0179494 A1 | 8/2007 | Faure | |
| 2007/0249911 A1 | 10/2007 | Simon | |
| 2007/0265491 A1 | 11/2007 | Krag et al. | |
| 2008/0108950 A1 | 5/2008 | Rioux et al. | |
| 2008/0110457 A1* | 5/2008 | Barry | A61M 25/10 |
| | | | 128/200.26 |
| 2009/0054805 A1* | 2/2009 | Boyle, Jr. | A61B 17/12159 |
| | | | 600/564 |
| 2009/0105745 A1 | 4/2009 | Culbert | |
| 2010/0036312 A1 | 2/2010 | Krolik et al. | |
| 2010/0069919 A1 | 3/2010 | Carls et al. | |
| 2010/0168821 A1 | 7/2010 | Johnson et al. | |
| 2010/0174306 A1 | 7/2010 | Mitelberg et al. | |
| 2010/0191279 A1* | 7/2010 | Kassab | A61B 17/12031 |
| | | | 606/213 |
| 2010/0274238 A1 | 10/2010 | Klimovitch | |
| 2010/0312141 A1 | 12/2010 | Keast et al. | |
| 2011/0105841 A1 | 5/2011 | Kutikov et al. | |
| 2011/0105947 A1 | 5/2011 | Fritscher-Ravens et al. | |
| 2011/0190764 A1 | 8/2011 | Long et al. | |
| 2012/0053566 A1 | 3/2012 | Tada et al. | |
| 2012/0071866 A1 | 3/2012 | Kerr et al. | |
| 2012/0071922 A1 | 3/2012 | Shanley et al. | |
| 2012/0109174 A1 | 5/2012 | Vetter | |
| 2012/0143020 A1 | 6/2012 | Bordoley et al. | |
| 2012/0253229 A1 | 10/2012 | Cage | |
| 2012/0289776 A1* | 11/2012 | Keast | A61B 5/062 |
| | | | 600/114 |
| 2012/0316608 A1 | 12/2012 | Foley | |
| 2013/0018414 A1 | 1/2013 | Widomski et al. | |
| 2013/0031735 A1* | 2/2013 | Brand | A61B 1/00131 |
| | | | 15/104.93 |
| 2013/0046140 A1 | 2/2013 | Pravong et al. | |
| 2013/0150701 A1 | 6/2013 | Budar et al. | |
| 2013/0190809 A1* | 7/2013 | Vidlund | A61B 17/0057 |
| | | | 606/213 |
| 2013/0197357 A1 | 8/2013 | Green et al. | |
| 2014/0236184 A1 | 8/2014 | Leimbach et al. | |
| 2014/0257359 A1 | 9/2014 | Tegels et al. | |
| 2014/0275979 A1 | 9/2014 | Fujimoto et al. | |
| 2014/0276009 A1 | 9/2014 | Boyle, Jr. | |
| 2014/0276687 A1 | 9/2014 | Goodman et al. | |
| 2014/0276732 A1 | 9/2014 | Strobl et al. | |
| 2014/0276911 A1 | 9/2014 | Smith et al. | |
| 2014/0277039 A1 | 9/2014 | Liberatore et al. | |
| 2014/0277071 A1 | 9/2014 | Wu et al. | |
| 2014/0343348 A1 | 11/2014 | Kaplan et al. | |
| 2015/0057570 A1 | 2/2015 | Chin et al. | |
| 2015/0112225 A1 | 4/2015 | Prow et al. | |
| 2015/0141981 A1 | 5/2015 | Price et al. | |
| 2015/0265331 A1* | 9/2015 | Fleury | A61B 18/04 |
| | | | 606/28 |
| 2015/0282823 A1 | 10/2015 | Trees et al. | |
| 2015/0342638 A1 | 12/2015 | Smith et al. | |
| 2016/0067465 A1 | 3/2016 | Gerrans et al. | |
| 2016/0192911 A1 | 7/2016 | Kassab et al. | |
| 2016/0192999 A1 | 7/2016 | Stulen et al. | |
| 2016/0206366 A1 | 7/2016 | Clauda et al. | |
| 2016/0220294 A1 | 8/2016 | Babkin et al. | |
| 2016/0367279 A1 | 12/2016 | Orphanos et al. | |
| 2017/0000553 A1 | 1/2017 | Wiener et al. | |
| 2017/0000554 A1 | 1/2017 | Yates et al. | |
| 2017/0042516 A1 | 2/2017 | Boyle, Jr. | |
| 2017/0202595 A1 | 7/2017 | Shelton, IV | |
| 2017/0281214 A1 | 10/2017 | Brown et al. | |
| 2018/0140319 A1 | 5/2018 | Saidi et al. | |
| 2018/0153604 A1 | 6/2018 | Ayvazyan et al. | |
| 2018/0193060 A1 | 7/2018 | Reddy et al. | |
| 2018/0235650 A1 | 8/2018 | Beaupre | |
| 2019/0000534 A1 | 1/2019 | Messerly et al. | |
| 2019/0038306 A1 | 2/2019 | Lindner et al. | |
| 2019/0076164 A1 | 3/2019 | Boyle, Jr. et al. | |
| 2019/0099197 A1 | 4/2019 | Boyle, Jr. et al. | |
| 2019/0201029 A1 | 7/2019 | Shelton, IV et al. | |

(56) References Cited

U.S. PATENT DOCUMENTS

| | | | |
|---|---|---|---|
| 2019/0246946 A1 | 8/2019 | Kopel et al. | |
| 2019/0269387 A1 | 9/2019 | Kerr | |
| 2019/0388132 A1 | 12/2019 | Azamian et al. | |
| 2020/0038089 A1 | 2/2020 | Cohn et al. | |
| 2020/0038090 A1 | 2/2020 | Cohn et al. | |
| 2020/0038097 A1 | 2/2020 | Cohn et al. | |
| 2020/0390427 A1* | 12/2020 | Eisenthal | A61B 17/00491 |
| 2021/0219967 A1 | 7/2021 | Cohn et al. | |
| 2021/0322091 A1* | 10/2021 | Addison | A61B 18/1477 |
| 2021/0338215 A1 | 11/2021 | Cohn et al. | |
| 2021/0338218 A1 | 11/2021 | Cohn et al. | |
| 2021/0338265 A1 | 11/2021 | Cohn et al. | |
| 2021/0338315 A1 | 11/2021 | Cohn et al. | |
| 2021/0378731 A1 | 12/2021 | Boateng et al. | |
| 2021/0393332 A1 | 12/2021 | Cohn et al. | |
| 2022/0031382 A1 | 2/2022 | Cohn et al. | |
| 2022/0047314 A1 | 2/2022 | Cohn et al. | |
| 2022/0047322 A1 | 2/2022 | Cohn et al. | |
| 2022/0225970 A1 | 7/2022 | Boyle, Jr. | |
| 2023/0380878 A1 | 11/2023 | Cohn et al. | |
| 2025/0228599 A1 | 7/2025 | Cohn et al. | |

FOREIGN PATENT DOCUMENTS

| | | | |
|---|---|---|---|
| DE | 102016101915 A1 | 8/2017 |
| EP | 1340469 A1 | 9/2003 |
| EP | 2866700 A1 | 5/2015 |
| EP | 3603546 A1 | 2/2020 |
| JP | H11244298 A | 9/1999 |
| JP | 3287788 B2 | 6/2002 |
| JP | 2003516800 A | 5/2003 |
| JP | 2004230054 A | 8/2004 |
| JP | 2004528056 A | 9/2004 |
| JP | 2007185495 A | 7/2007 |
| JP | 2008538518 A | 10/2008 |
| JP | 2009536083 A | 10/2009 |
| JP | 2012500098 A | 1/2012 |
| JP | 2012183302 A | 9/2012 |
| JP | 2013509255 A | 3/2013 |
| JP | 2014030555 A | 2/2014 |
| JP | 2014113211 A | 6/2014 |
| JP | 2018118115 A | 8/2018 |
| JP | 2019505320 A | 2/2019 |
| JP | 2020018853 A | 2/2020 |
| JP | 2020506772 A | 3/2020 |
| WO | WO-9603163 A1 | 2/1996 |
| WO | WO-2005110508 A2 | 11/2005 |
| WO | WO-2006108067 A2 | 10/2006 |
| WO | WO-2007014313 A2 | 2/2007 |
| WO | WO-2010001405 A1 | 1/2010 |
| WO | WO-2011053648 A1 | 5/2011 |
| WO | WO-2011094110 A1 | 8/2011 |
| WO | WO-2014172396 A2 | 10/2014 |
| WO | WO-2018144898 A1 | 8/2018 |
| WO | WO-2018218210 A1 | 11/2018 |
| WO | WO-2019130110 A1 | 7/2019 |
| WO | WO-2019239338 A2 | 12/2019 |
| WO | WO-2020006660 A1 | 1/2020 |
| WO | WO-2021220220 A1 | 11/2021 |
| WO | WO-2021220221 A2 | 11/2021 |
| WO | WO-2021220222 A2 | 11/2021 |
| WO | WO-2021220223 A1 | 11/2021 |
| WO | WO-2021220224 A2 | 11/2021 |
| WO | WO-2021220225 A1 | 11/2021 |
| WO | WO-2021250526 A1 | 12/2021 |
| WO | WO-2021260468 A1 | 12/2021 |
| WO | WO-2022023998 A1 | 2/2022 |
| WO | WO-2022034412 A1 | 2/2022 |
| WO | WO-2022038433 A1 | 2/2022 |
| WO | WO-2022214896 A1 | 10/2022 |

OTHER PUBLICATIONS

International Preliminary Report on Patentability and Written Opinion for International Application No. PCT/IB2021/053589 dated Oct. 27, 2022, 5 pages.

International Preliminary Report on Patentability and Written Opinion for International Application No. PCT/IB2021/053590 dated Oct. 27, 2022, 9 pages.

International Search Report and Written Opinion for Application No. PCT/IB2021/053591, mailed Jul. 27, 2021, 14 pages.

Non final office action for U.S. Appl. No. 17/201,116, mailed Jun. 22, 2023, 11 pages.

Non final office action for U.S. Appl. No. 17/201,122, mailed May 12, 2023, 17 pages.

Non-Final Office Action for U.S. Appl. No. 17/201,166 dated Feb. 14, 2023, 28 pages.

Office Action for European Application No. 21723411.1 mailed Jul. 31, 2024, 5 pages.

Final Office Action for U.S. Appl. No. 17/201,166 dated Nov. 27, 2023, 24 pages.

Notification of Reasons for Rejection for Japanese Application No. 2022-566611 mailed Feb. 4, 2025, with English translation 17 pages.

Office Action for European Application No. 21723411.1 mailed Nov. 27, 2024, 13 pages.

Final Office Action for U.S. Appl. No. 17/319,827 dated Aug. 6, 2025, 9 pages.

Office Action for Japanese Application No. 2022-566611 mailed Jul. 15, 2025, with English translation, 12 pages.

\* cited by examiner

502 — Anchor to target site

306 — Dispose sealing device adjacent target site

308 — Seal target site

310 — Dispose fill material at target site 1000
1001
1002
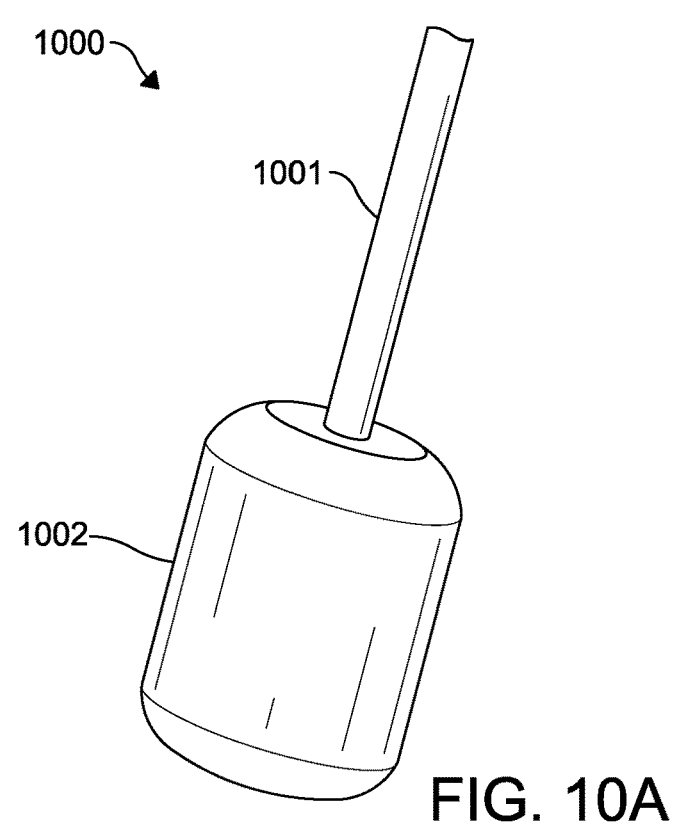
FIG. 10A
1000
1001
1002
1000
1002
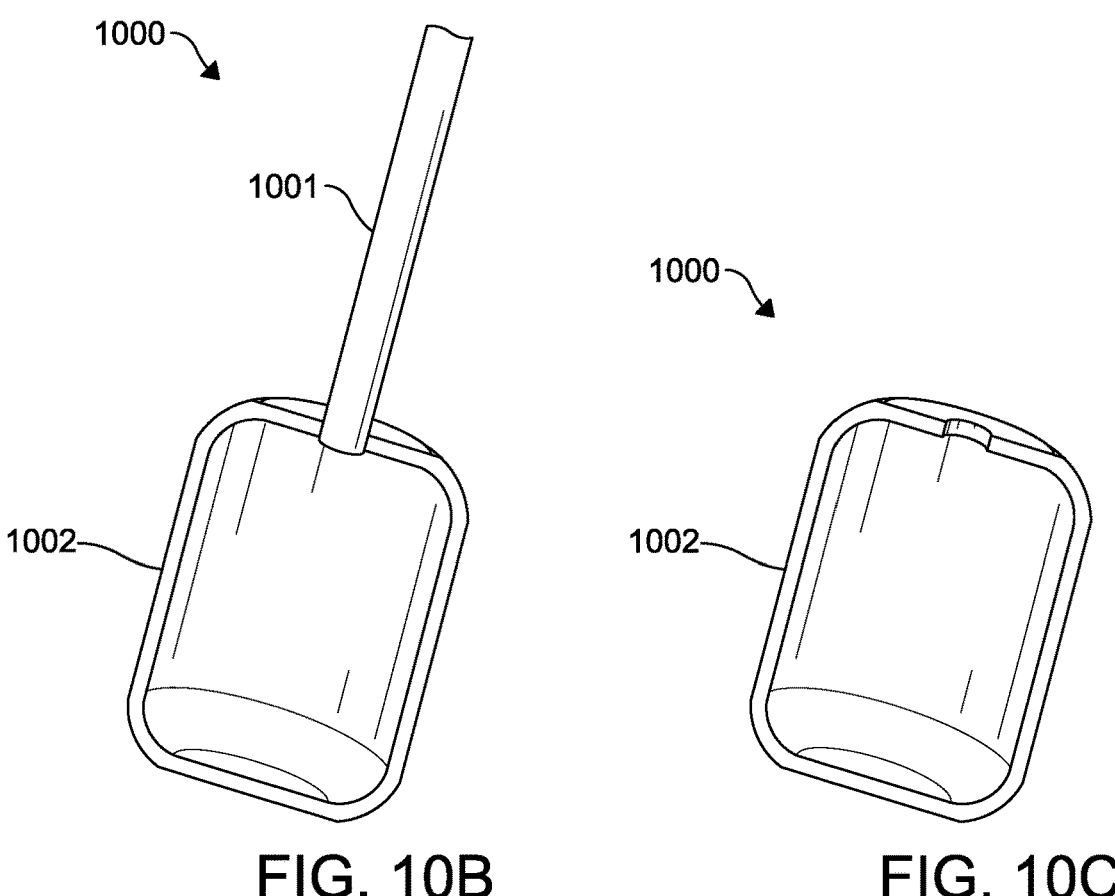
FIG. 10B                    FIG. 10C

1422

1424

1420

1605 1605 1605

1510

1515

1510

1802 — Core Tissue at a Target Site

1804 — Dispose Port at the Target Site

1806 — Anchor an Anchor Device to the Target Site

1808 — Disposing a Sealing Device via the Port

1810 — Causing the Sealing Device to Seal

SYSTEMS AND METHODS FOR SEALING CORED OR PUNCTURED TISSUE USING INFLATABLE BALLOON

CROSS-REFERENCE TO RELATED APPLICATIONS

This application claims priority to and the benefit of U.S. Patent Application No. 63/017,734 filed Apr. 30, 2020, which is hereby incorporated by reference in their entirety.

BACKGROUND

Tissue, such as lung tissue, may become punctured or may have a portion removed. Removal of tissue may include a surgery that involves coring and removal of a tissue specimen, for example, from the lung. However, problems may arise with cored or punctured tissue. Improvements are needed in managing cored or puncture tissue, such as lung tissue.

SUMMARY

It may be desirable to remove a core of tissue from target tissue sites including, but not limited to, the lungs, the liver, pancreas, or gastrointestinal (GI) tract, for which managing post-coring bleeding may be desired. A core of tissue may have a prescribed (e.g., pre-defined) shape (e.g., columnar) and dimension based on a coring apparatus. Such coring apparatus may be used to core the same or substantially the same shaped tissue core in a repeatable manner. Such coring may be distinguished from other tissue removal, for example using scissors or scalpel, where the cut tissue will not have a pre-defined shape or dimensions.

Once cored, it may be desirable to seal the cored tissue. As described herein sealing may be desirable during a coring process, for example, to seal blood and/or fluid flow at the core site that may be caused from the coring operation itself. Additionally or alternatively, sealing may be desirable after a core of tissue and/or a coring device is removed. Moreover, sealing may occur at least once during a coring process and at least once after a core of tissue and/or a coring device is removed. As an illustrative example, the cored site may be sealed during a coring process to limit undesired blood or fluids from entering the cored site. Then, the cored site may be sealed after the tissue core is removed to limit undesired air to escape through the cored site, such as in the lungs. Various sealing operations may be used.

Systems and/or methods for sealing tissue are described herein. A method for sealing tissue at a cored site may comprise coring tissue at a target site such that a tissue core is removed from the target site thereby creating a core cavity at the target site. A sealing device may be disposed adjacent the target site. The sealing device may be caused to seal at least a portion of the core cavity at the target site. The sealing device may be spaced (e.g., removed, separated, etc.) from the target site.

Systems and/or methods for sealing tissue are described herein. An example method may comprise disposing a port to provide access to a target site. Example methods may comprise anchoring an anchor device, via the port, to a surface at the target site. Example methods may comprise disposing, via the port, a sealing device adjacent the target site. Example methods may comprise causing the sealing device to seal the target site. Example methods may comprise disposing a fill material adjacent the target site. The sealing device may minimize escape of the fill material from the target site.

Systems and/or methods for sealing tissue are described herein. An example method may comprise disposing a sealing device adjacent a target site of a lung, while the lung is collapsed. Example methods may comprise causing the sealing device to seal the target site. Example methods may comprise disposing a fill material adjacent the target site. The sealing device may minimize escape of the fill material from the target site. Example methods may comprise spacing (e.g., removing, separating, etc.) the sealing device from the target site.

Systems and/or methods for sealing tissue are described herein. An example method may comprise anchoring an anchor device to a surface at a target site. Example methods may comprise disposing, using the anchoring, a sealing device adjacent the target site. Example methods may comprise causing the sealing device to seal the target site. Example methods may comprise disposing a fill material adjacent the target site. The sealing device may minimize escape of the fill material from the target site.

Systems and/or methods for sealing tissue are described herein. An example method may comprise disposing a fluid delivery device into a target site of a lung. Example methods may comprise disposing a fill material into the target site. Example methods may comprise spacing (e.g., removing, separating, etc.) the fluid delivery device from the target site.

BRIEF DESCRIPTION OF THE DRAWINGS

The following drawings show generally, by way of example, but not by way of limitation, various examples discussed in the present disclosure. In the drawings:

FIGS. 10A, 10B, and 10C show an application of an example system for sealing tissue.

DETAILED DESCRIPTION

Figure 1:
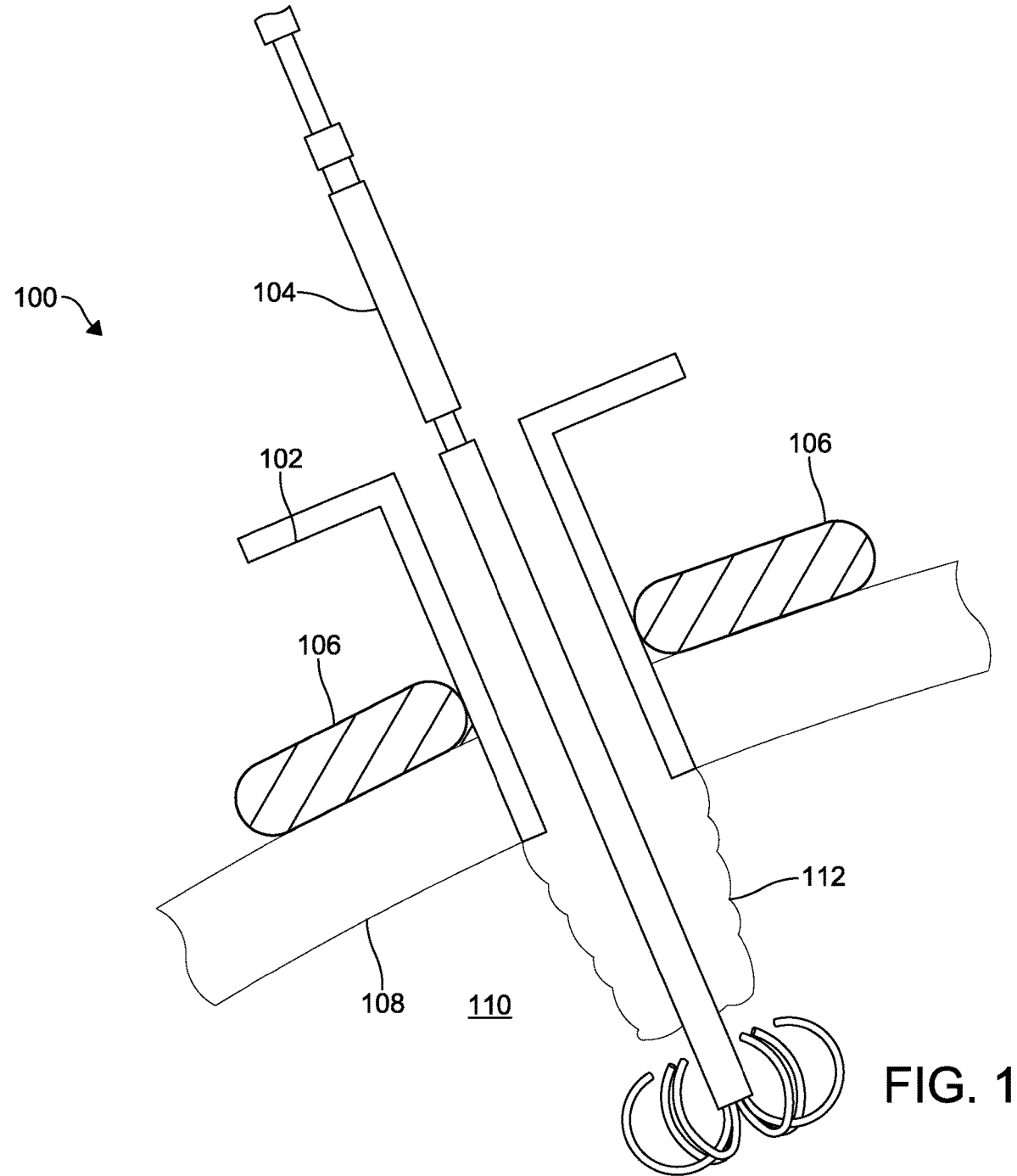
FIG. 1 shows an application of an example system for sealing tissue.

The present disclosure relates to systems and methods for treatment of tissue such as cored tissue, punctured tissue, and/or a removed tissue region. Other tissue and sites may benefit from the disclosed systems and methods.

The present disclosure relates to methods and systems for coring tissue and sealing the core cavity created by removing the tissue core. Such methods may comprise disposing a fill material in the core cavity. Methods may comprise applying pressure to a portion of the core cavity such as to a wall defining the core cavity. Methods may comprise ablating a portion of the core cavity such as a wall defining the core cavity. Methods may comprise causing a cavity closure device, such as suture thread, a stapling device, an ultrasonic tissue sealing device, a bipolar radiofrequency sealing device, or any combination thereof to close the tissue cavity. Methods may comprise disposing a cavity sealing material, such as a tissue graft, a hemostatic patch, a hemostatic agent such as fibrin or thrombin, a biological adhesive material such as Dermabond®, or any combination thereof to close the tissue cavity.

Methods may comprise any combination or permutation of: 1) disposing an anchoring device into a tissue cavity, 2) disposing a tissue access port into the tissue cavity, 3) disposing a tissue sealing device into the tissue cavity (with or without a tissue access port, with or without guidance from an anchoring device), 4) causing the tissue sealing device to seal at least a portion of the tissue cavity, 5) introducing a fill material into the tissue cavity (with or without a fill material delivery device, with or without being preceded by disposing a tissue sealing device into the tissue cavity, with or without removing the tissue sealing device after sealing at least a portion of the tissue cavity, with or without a tissue access port), 6) disposing a cavity sealing material adjacent to the tissue cavity (with or without being preceded by disposing a tissue sealing device into the tissue cavity, with or without removing the tissue sealing device after sealing at least a portion of the tissue cavity, with or without being preceded by introducing a fill material into the tissue cavity), 7) disposing a cavity closure device adjacent to the tissue, and 8) causing a cavity closure device to close the tissue cavity (with or without being preceded by any combination or permutation of the above steps). As described herein, methods may be used to core and/or seal tissue at various target sites. Although a lung is used as an illustrative example, it should not be so limiting, as other target sites may be punctured or actively cored and may benefit from the disclosed sealing methods.

The present disclosure relates to a method to deliver a fill material such as autologous blood to the core site that may be used to seal and provide pneumostasis. As an example, once the tissue specimen is cored and removed from the lung, there may be a need to seal the core site to provide pneumostasis. As a further example, pneumostasis may be achieved in the same surgery session as the tissue removal.

Although autologous blood is described herein as an example, other fill materials and additives may be used. For example, a hemostatic adjunct such as an absorbable gelatin foam (e.g., SURGIFOAM®), biologic, oxidized regenerated cellulose (ORC), fibrin/thrombin spray, etc. As a further example, a patient may have a rare disorder of hemophilia in which their blood does not clot normally. Other patients might be on blood thinning medicines which could inhibit blood clotting formation. For such patients, to seal the cored cavity, thrombin and/or fibrinogen may be added to the autologous blood sample to aid in clot formation. Reactive polyethylene glycol (PEG), ammonium sulfate, ethanol, calcium chloride, or magnesium chloride may also be added to the blood sample to aid in clot formation. Another source for the blood to be used to seal the cored cavity is donated blood from other people or blood bank. Donated blood may be used with or without clotting agents as mentioned above.

Systems and/or methods for sealing tissue are described herein. An example method may comprise disposing a port to provide access to a target site. The target site may comprise biological tissue. The target site may comprise tissue of a lung. The target site may comprise a cored tissue. The target site may comprise a punctured tissue. Other sites may benefit from the disclosed methods.

Example methods may comprise anchoring an anchor device (e.g., via the port) to a surface at the target site. Anchoring may be performed by any suitable structure for securing the device to the lung. Example methods may comprise disposing (e.g., via the port) a sealing device adjacent the target site. Example methods may comprise disposing a sealing device adjacent the target site using the anchoring device as a guide. The sealing device may comprise an inflatable balloon. The sealing device may comprise an inflatable balloon with an array of radio frequency (RF) electrodes configured to ablate and seal tissue. The sealing device may comprise an inflatable balloon configured to seal tissue using a thermal fluid. The sealing device may comprise an inflatable balloon catheter. The sealing device may comprise an access port with an array of RF electrodes configured to ablate and seal tissue. The sealing device may comprise at least one microwave ablation probe.

Example methods may comprise causing the sealing device to seal the target site. The causing the sealing device to seal the target site may comprise causing at least a portion of the sealing device to abut a portion of the target site. Example methods may comprise disposing a fill material adjacent the target site. Example methods may comprise disposing a fill material adjacent the target site via a fill material delivery device such as a catheter. The fill material may comprise autologous blood, donated blood, recirculated blood, hemostatic adjuncts such as fibrin and/or thrombin, biological tissue adhesives such as Dermabond®, ORC, absorbable gelatin, or any combination thereof. The fill material may promote pneumostasis. The fill material may additionally promote hemostasis. Other materials may be used. The sealing device may minimize escape of the fill material from the target site.

As an illustrative example, the target site may comprise at least a portion of a lung. The lung may be caused to collapse prior to disposing the sealing device adjacent the target site. The lung may be allowed to ventilate while the sealing device is sealing the target site. The sealing device may be spaced (e.g., removed, separated, etc.) from the target site after the fill material is disposed.

Systems and/or methods for sealing are described herein. An example method may comprise disposing a sealing device adjacent a target site of a lung. The sealing device may be disposed adjacent the target site while the lung is collapsed. However, the lung may be ventilated. Example methods may comprise causing the sealing device to seal the target site. Example methods may comprise disposing a sealing device adjacent the target site using the anchoring device as a guide. The sealing device may comprise an inflatable balloon. The sealing device may comprise an inflatable balloon with an array of RF electrodes configured to ablate and seal tissue. The sealing device may comprise an inflatable balloon configured to seal tissue using a thermal fluid. The sealing device may comprise an inflatable balloon catheter. The sealing device may comprise an access port with an array of RF electrodes configured to ablate and seal tissue. The sealing device may comprise at least one microwave ablation probe. Example methods may comprise disposing a fill material adjacent the target site. Example methods may comprise disposing a fill material adjacent the target site via a fill material delivery device such as a catheter. The fill material may comprise autologous blood, donated blood, recirculated blood, hemostatic adjuncts such as fibrin, thrombin, biological tissue adhesives such as Dermabond®, ORC, absorbable gelatin, or any combination thereof. The fill material may promote pneumostasis. The fill material may additionally promote hemostasis. Other materials may be used. The sealing device may minimize escape of the fill material from the target site.

Systems and/or methods for sealing are described herein. An example method may comprise disposing a fluid delivery device into a target site of a lung. The sealing device may be disposed adjacent the target site while the lung is collapsed. The sealing device may be disposed adjacent the target site while the lung is ventilated. Example methods may comprise disposing a fill material into the target site. Example methods may comprise spacing (e.g., removing, separating, etc.) the sealing device from the target site.

The sealing device may comprise an inflatable balloon. The sealing device may comprise an inflatable balloon with an array of RF electrodes configured to ablate and seal tissue. The sealing device may comprise an inflatable balloon configured to seal tissue using a thermal fluid. The sealing device may comprise an inflatable balloon catheter. The sealing device may comprise an access port with an array of RF electrodes configured to ablate and seal tissue. The sealing device may comprise at least one microwave ablation probe. The systems and/or methods described herein may allow clotted blood to provide a seal to achieve pneumostasis. Example methods may comprise disposing a fill material adjacent the target site. Example methods may comprise disposing a fill material adjacent the target site via a fill material delivery device such as a catheter. The fill material may comprise autologous blood, donated blood, recirculated blood, hemostatic adjuncts such as fibrin, thrombin, biological tissue adhesives such as Dermabond®, ORC, absorbable gelatin, or any combination thereof. The fill material may promote pneumostasis. The fill material may additionally promote hemostasis. Other materials may be used. The sealing device may minimize escape of the fill material from the target site.

The target site may comprise a cavity. The cavity may be closed, for example, after sealing. Closing the cavity may comprise using biological tissue adhesive such as Dermabond®, tissue grafts, hemostatic sealing patches, staple closure, sutures, or the like.

Figure 6:
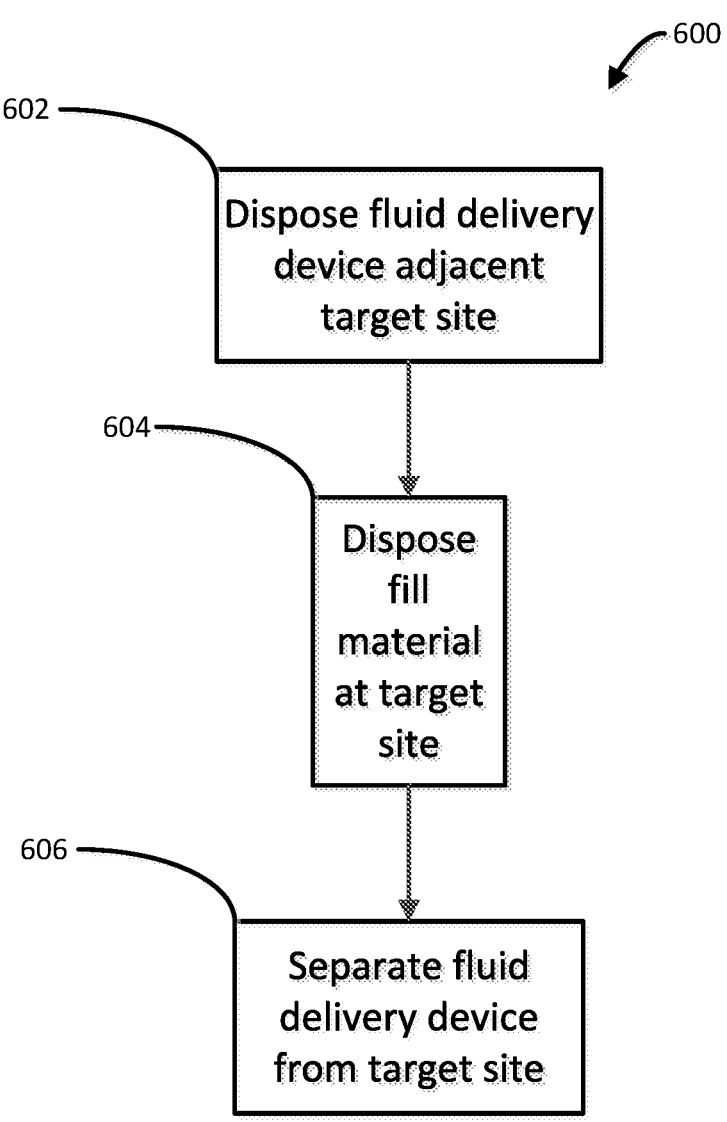
FIG. 6 shows a flow diagram of an example method for sealing tissue.

FIG. 1 shows an example system 100. The system 100 may comprise a port such as chest port 102 configured to provide access, such as via a channel to a portion of a body. It should be understood that various channels or ports may be used throughout the body and the chest port 102 is shown as a non-limiting example. As an illustrative example, the chest port 102 is shown disposed adjacent ribs 106 to provide access to lungs 110 of a patient. However, other sites may be used and a chest port 102 (or other port) may not be necessary. An anchor device 104 may be anchored to tissue, such as the lung 110. An example anchor device is shown in FIG. 6 for illustration. However, any suitable device for anchoring to the target site 112 may be used. As show, the anchor device 104 extends via the chest port 102, through the pleura 108, and anchors to tissue in the lung 110. The anchor device 104 may be anchored (e.g., releasably coupled) to a tissue at a target site 112. The target site 112 may comprise a core site where a portion of lung tissue has been cored, punctured, or removed. The anchor device 104 may be placed at the target site 112 while the lung is inflated. However, other processes may be implemented while the lung is collapsed.

Figure 2:
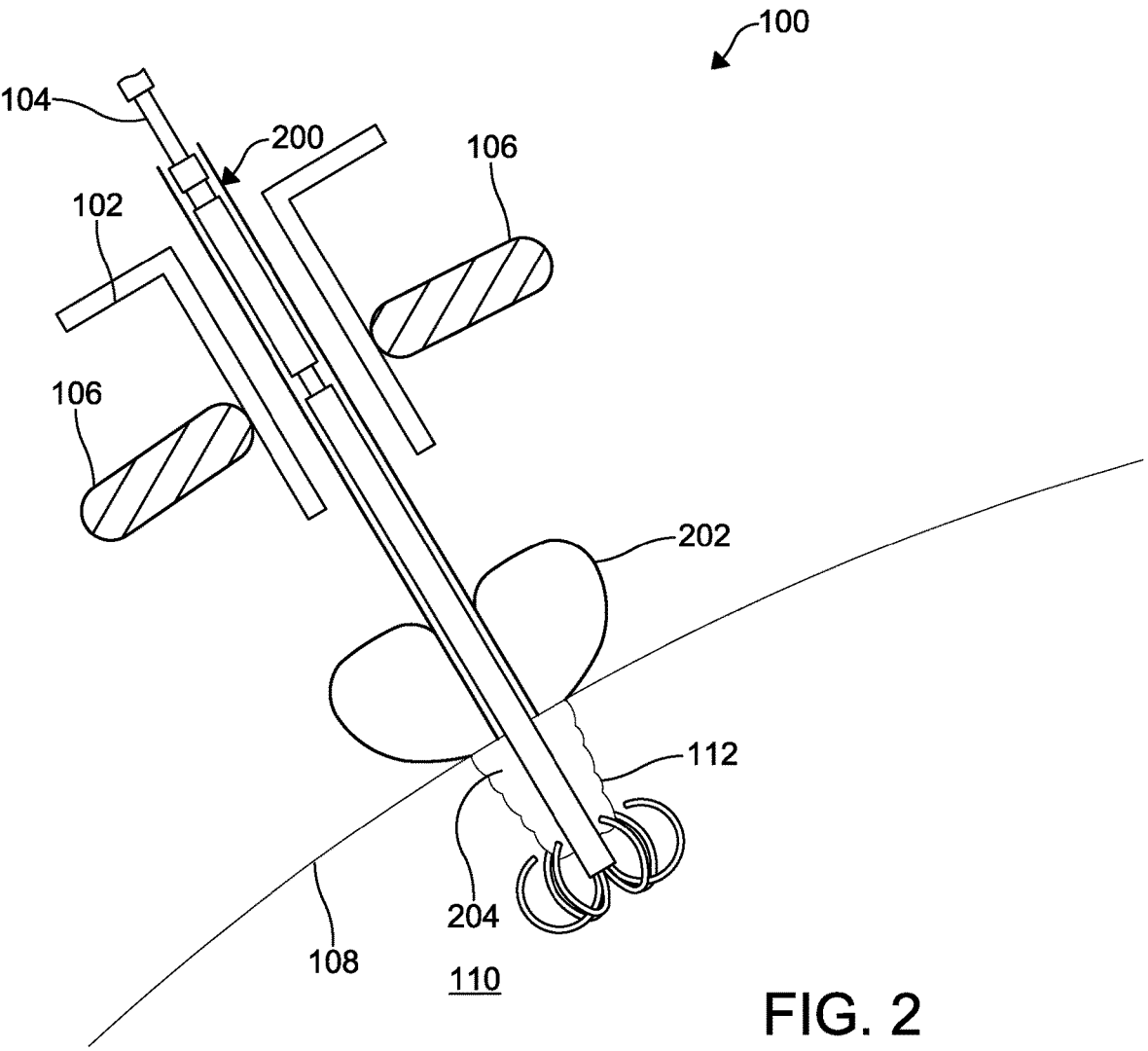
FIG. 2 shows an application of an example system for sealing tissue.

FIG. 2 shows an application of an example sealing device 200. The sealing device 200 may comprise an inflatable balloon 202. Other sealing mechanisms may be used. The sealing device 200 may comprise and/or be in contact with a balloon catheter. The balloon catheter may be a single lumen balloon catheter. The balloon catheter may be multi-lumen balloon catheter. The sealing device 200 may be disposed adjacent the target site 112. As such, the sealing device 200 may seal the target site 112 to minimize exit of a fluid or material from the target site 112. As an example, a fill material 204 may be disposed at the target site 112 and may be sealed in the target site 112 by the sealing device 200. As an illustrative example, the inflatable balloon 202 may provide sealing while the lung 110 moves (e.g., inflates and deflates). The sealing device 200 may be implemented when the lung 110 is inflated or collapsed.

Figure 3:
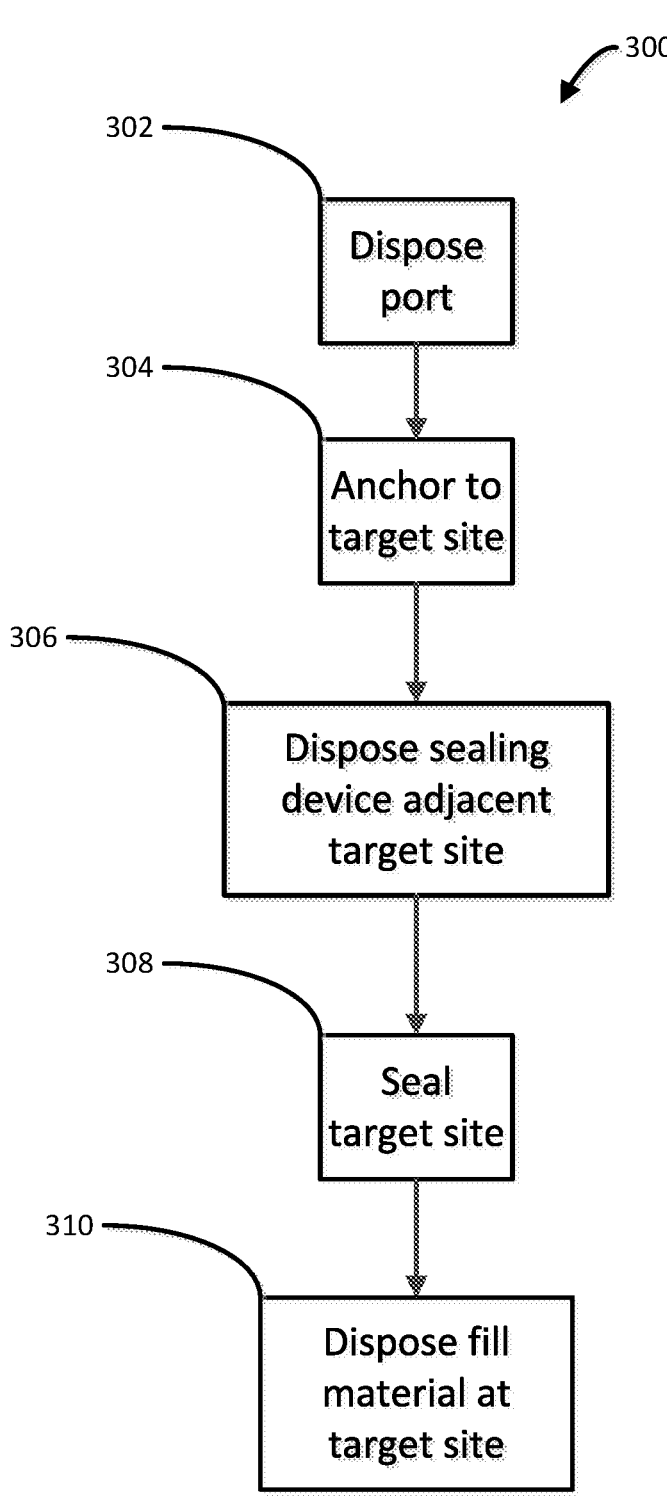
FIG. 3 shows a flow diagram of an example method for sealing tissue.

FIG. 3 shows a flow diagram of an example method 300. At 302, a port may be disposed to provide access to a target site. A port (e.g., chest port 102 (FIG. 1)) may be disposed to provide access to a target site. A user may dispose a port to provide access to a target site. The target site may comprise biological tissue. The target site may comprise tissue of a lung. The target site may comprise a cored tissue. The target site may comprise a punctured tissue. The target site may comprise at least a portion of a lung.

At 304, an anchor device may be anchored to a surface at the target site. As an example, a user may anchor the anchor device, via the port, to a surface at the target site.

At 306, a sealing device may be disposed adjacent the target site, for example via the port. The sealing device may comprise an inflatable balloon. The sealing device may comprise an inflatable balloon catheter. The lung may be caused to collapse prior to disposing the sealing device adjacent the target site. The lung may be allowed to ventilate while the sealing device is sealing the target site.

At 308, the sealing device may be caused to seal the target site. Causing the sealing device to seal the target site may comprise causing at least a portion of the sealing device to abut a portion of the target site.

At 310, a fill material may be disposed adjacent the target site. The sealing device may minimize escape of the fill material from the target site. The fill material may promote pneumostasis. The fill material may comprise autologous blood. The sealing device may be spaced (e.g., removed, separated, etc.) from the target site after the fill material is disposed.

Figure 4:
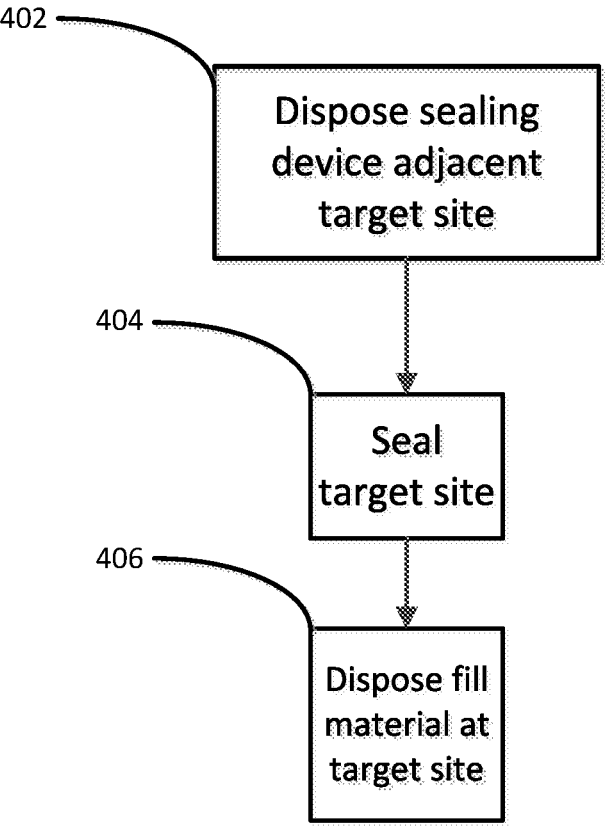
FIG. 4 shows a flow diagram of an example method for sealing tissue.

FIG. 4 shows a flow diagram of an example method 400. At 402, a sealing device may be disposed adjacent a target site of a lung, while the lung is collapsed. The target site may comprise tissue of a lung. The target site may comprise a cored tissue. The target site may comprise a punctured tissue. The sealing device may comprise an inflatable balloon. The sealing device may comprise an inflatable balloon catheter.

At 404, the sealing device may be caused to seal the target site. Causing the sealing device to seal the target site may comprise causing at least a portion of the sealing device to abut a portion of the target site.

At 406, a fill material may be disposed adjacent the target site. The sealing device may minimize escape of the fill material from the target site. The fill material may promote pneumostasis. The fill material may comprise autologous blood. At 408, the sealing device may be spaced (e.g., removed, separated, etc.) from the target site.

Figure 5:
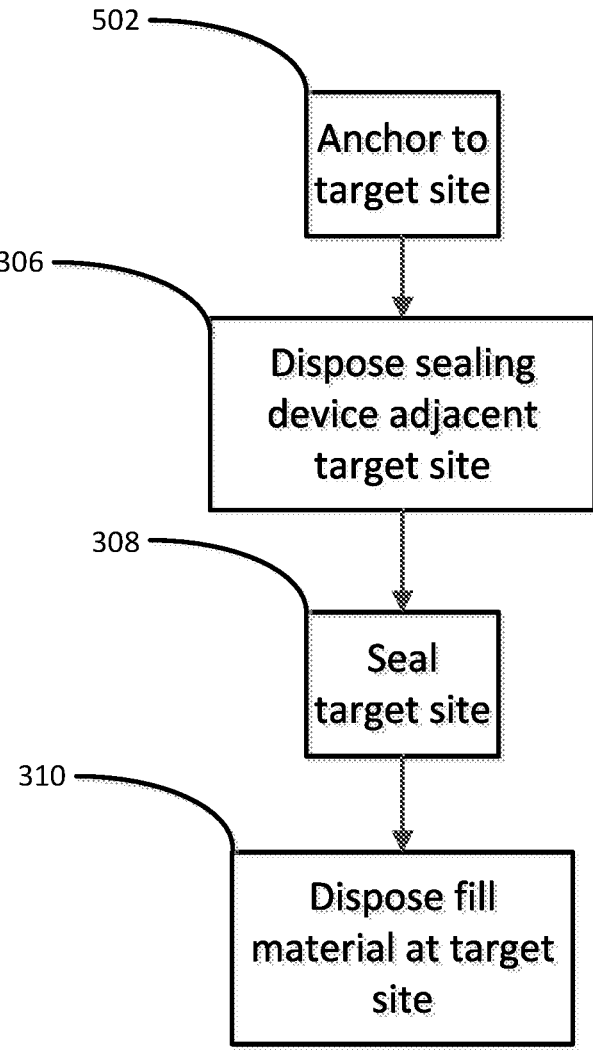
FIG. 5 shows a flow diagram of an example method for sealing tissue.

FIG. 5 shows a flow diagram of an example method 500. At 502, an anchor device may be anchored to a surface at a target site. The target site may comprise biological tissue. The target site may comprise tissue of a lung. The target site may comprise a cored tissue. The target site may comprise a punctured tissue. The target site may comprise at least a portion of a lung.

At 504, a sealing device may be disposed adjacent the target site using the anchoring. The sealing device may comprise an inflatable balloon. The sealing device may comprise an inflatable balloon catheter. The lung may be caused to collapse prior to disposing the sealing device adjacent the target site.

At 506, the sealing device may be caused to seal the target site. Causing the sealing device to seal the target site may comprise causing at least a portion of the sealing device to abut a portion of the target site. The lung may be allowed to ventilate while the sealing device is sealing the target site.

At 508, a fill material may be disposed adjacent the target site. The sealing device may minimize escape of the fill material from the target site. The fill material may promote pneumostasis. The fill material may comprise autologous blood. The sealing device may be spaced (e.g., removed, separated, etc.) from the target site after the fill material is disposed.

FIG. 6 shows a flow diagram of an example method 600. At 602, a fluid delivery device may be disposed adjacent or into a target site of a lung, while the lung is collapsed. The target site may comprise biological tissue. The target site may comprise tissue of a lung. The target site may comprise cored tissue. The target site may comprise punctured tissue. The target site may comprise at least a portion of a lung.

At 604, a fill material may be disposed into the target site. The fill material may promote pneumostasis. The fill material may comprise autologous blood.

At 606, the fluid delivery device may be spaced (e.g., removed, separated, etc.) from the target site. The lung may be caused to collapse prior to disposing the fluid delivery device adjacent the target site.

Figure 7:
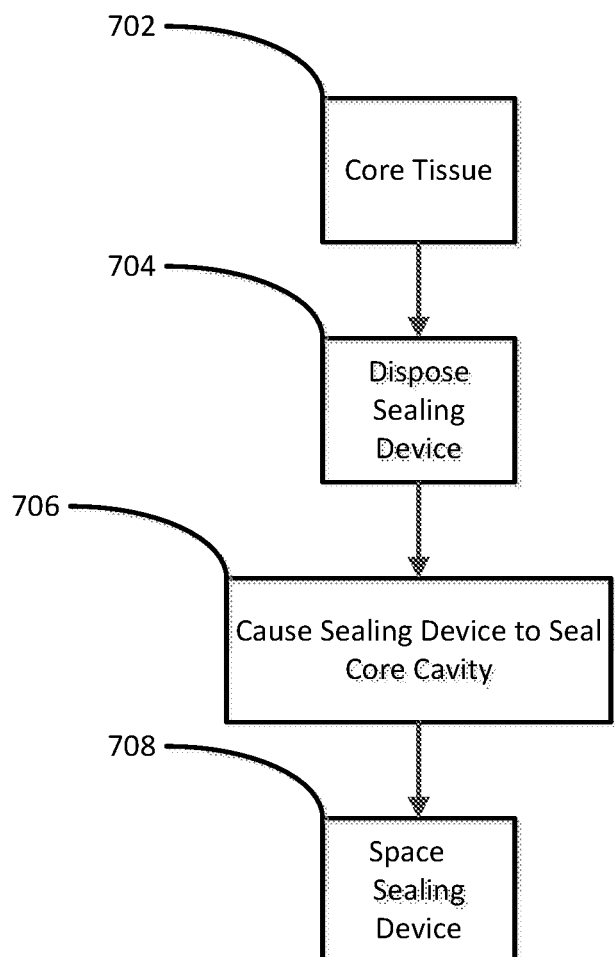
FIG. 7 shows a flow diagram of an example method for coring and for sealing tissue.

FIG. 7 shows a flow diagram of an example method. At 702, tissue at a target site may be cored such that a tissue core is removed from the target site thereby creating a core cavity at the target site. Coring tissue at a target site may comprise transecting and sealing tissue. Coring tissue at a target site may comprise disposing a tissue coring apparatus adjacent to a target tissue site. The tissue coring apparatus may comprise a first clamping element comprising a helical coil, a second clamping element, the second clamping element being positioned to oppose at least a portion of the first clamping element, a first and second electrode configured for the delivery of radiofrequency energy for sealing tissue, and/or a cutting element configured for the transection of at least a portion of the sealed tissue. Other apparatus may be used.

Coring tissue at a target site may comprise using the tissue coring apparatus to form the tissue core. The target site may be a tissue site such as a lung, for example. At 704, a sealing device may be disposed adjacent the target site. The sealing device may comprise an inflatable balloon. The sealing device may comprise an inflatable balloon catheter. At 706, the sealing device may be caused to seal at least a portion of the core cavity at the target site. Example sealing procedures are described herein and include fill materials, ablation, mechanical pressure, energy emission (e.g., RF energy), and others, for example. Causing the sealing device to seal at least a portion of the core cavity at the target site may comprise causing at least a portion of the sealing device to abut a wall defining the core cavity. Causing the sealing device to seal at least a portion of the core cavity at the target site may comprise ablating a wall defining the core cavity. Causing the sealing device to seal at least a portion of the core cavity at the target site may comprise applying pressure to a wall defining the core cavity. The method 700 may further comprise disposing a fill material in the core cavity, wherein the sealing device minimizes escape of the fill material from the core cavity. The fill material may comprise autologous blood. As an example, the target site may comprise at least a portion of a lung and the method may further comprise causing the lung to collapse prior to disposing the sealing device adjacent the target site. As a further example, the target site may comprise at least a portion of a lung and the method 700 may further comprise allowing the lung to ventilate while the sealing device is sealing the target site. At 708, the sealing device may be spaced (e.g., removed, separated, etc.) from the target site.

An example system for implementing one or more of the methods of the present disclosure may comprise a guided anchor. The example system may comprise a single lumen balloon catheter. The example system may comprise a multi-lumen balloon catheter. The example system may comprise a coring device. Post coring by the coring device, an anchor may be introduced into the tissue cavity to ensure access to a cored site, as shown in FIG. 1. The chest port may be removed, and the lung may be collapsed. The balloon catheter may be inserted over the anchor. Once the balloon catheter is in the chest cavity, the balloon catheter may be inflated. The inflated balloon catheter may be moved forward and pushed slightly against lung tissue. Autologous blood may be injected into a core site through the inflated balloon catheter. The inflated balloon catheter and autologous blood may be held in place for a predetermined time period (e.g., one (1) minute, etc.) to allow the blood to clot at the core site, as shown in FIG. 2. The lung may be allowed to resume ventilation. The inflated balloon catheter may be allowed to go up and down with the lung while maintaining contact with the lung to keep the blood at the core site to facilitate further clotting. The balloon catheter may be deflated. The balloon catheter and anchor may be removed after a predetermined time period (e.g., three (3) minutes, etc.). The autologous blood may be clotted at the core site to provide pneumostasis.

In an embodiment, the anchor and/or the balloon catheter may be used to deposit autologous blood at the core site with the lung collapsed. The anchor and/or the balloon catheter may be removed right after the autologous blood is delivered. The blood may be allowed to clot in place with a predetermined time period (e.g., five (5) minutes, etc.) before the lung is allowed to resume ventilation.

The example system may cause autologous blood to be delivered to the core site. Other fill materials may be used.

The example system may allow clotted blood to provide a seal to achieve pneumostasis.

Figure 8A:
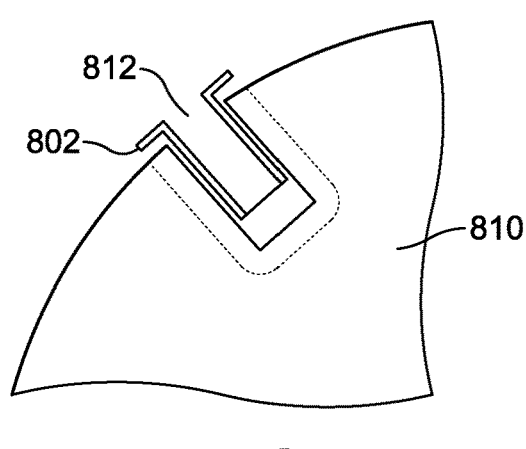
FIGS. 8A, 8B, and 8C show an application of an example system for sealing tissue.
Figure 8B:
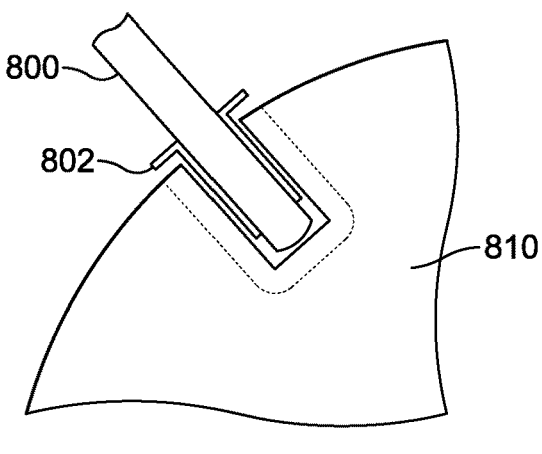
Figure 8C:
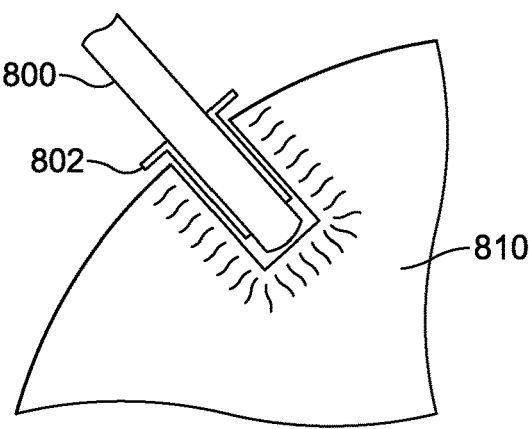

FIGS. 8A-8C show an example application. As shown, once a target site has been cored out and the tissue core removed, there may be a need to ablate the tissue wall of the cavity. As such, the following ablation methods could be used. For example, a rotating ablation probe may be used. FIG. 8A shows a cored-out cavity 812 in tissue 810 with the cavity sheath 802 in place to keep the cavity open. A rotating probe 800 is then inserted into the cavity sheath as shown in FIG. 8B. The probe 800 may be equipped with an energy source such as an array of energy heads or a continuous energy strip. The energy may be microwave, RF, other output form. Once the probe 800 is in place, the cavity sheath 802 may remain in place or be removed. The energy is then applied while the probe/energy heads are rotated to give a radially continuous ablation on the wall and bottom tissue 810 of the cavity as shown in FIG. 8C.

Figure 9A:
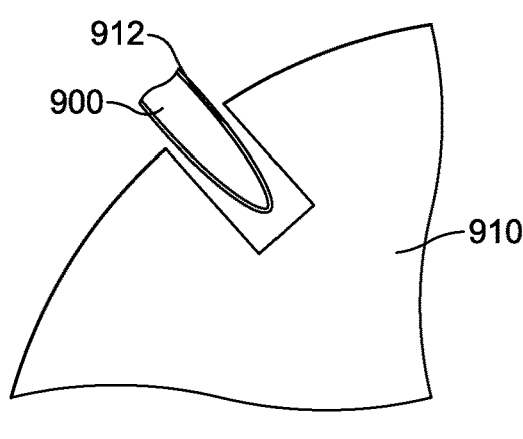
FIGS. 9A and 9B show an application of an example system for sealing tissue.
Figure 9B:
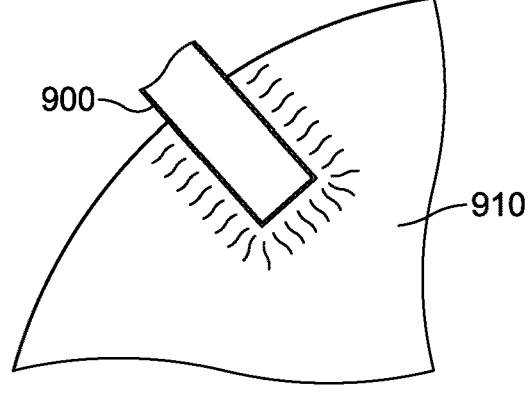

FIGS. 9A-9B show an example application. As shown, a hot balloon catheter may be used. For example, a balloon catheter 900 may be placed into a cavity 912 formed in tissue 910 and a cavity sheath may be removed to expose the cavity 912 needing to be ablated, as shown in FIG. 9A. The balloon 900 may then be inflated with hot fluid or hot air/gas to ablate the cavity wall tissue 910, as shown in FIG. 9B.

FIGS. 8-9 shown illustrative examples, but other methods of ablation or energy emission may be used for sealing tissue. For example, a shaped mesh catheter may be used. As such, a catheter with collapsed meshed shape may be inserted into the cavity and the cavity sheath is removed. The mesh may then be expanded, and suction may be applied to pull tissue to contact with the mesh. Energy, e.g. RF energy, may then be applied to ablate the cavity tissue wall.

FIGS. 10A-10C show an example application. As shown, once a target site has been cored out and the tissue core removed, there may be a need to seal the cut tissue wall of the cavity. As such, the following example procedure may be used. A device 1000 may comprise a fluid conduit 1001 and an inflatable absorbable balloon 1002. The balloon 1002 may be coated on the exterior with absorbable bio adhesive that will seal against the tissue of the cored cavity post coring, as shown in FIGS. 10A-10B. Once the deflated balloon 1002 may be placed in the desired location, the balloon 1002 may be inflated with CO2 (or other fluid), for example via fluid conduit 1001, so that the bio adhesive may press against the tissue wall of the cored cavity to achieve sealing to prevent air leak. The CO2 filled balloon 1002 may be pressurized to an appropriate pressure and may be left behind inside the cored cavity, as shown in FIG. 10C.

Various methods, devices, and systems may be used to core or remove tissue.

A method for removing a tissue lesion may comprise introducing a tissue resection device to a target tissue site, causing the tissue resection device to resect a core of tissue from the target tissue site, and removing the core of tissue from the body. The core of tissue may comprise at least a portion of a tissue lesion. A method may further comprise creating a core cavity at the target tissue site. A method may further comprise inserting a sleeve into the core cavity. A method may further comprise delivering radiofrequency energy through the core cavity. A method may further comprise delivering chemotherapy through the core cavity. A method may further comprise delivering microwave radiation through the core cavity. A method may further comprise delivering thermal energy through the core cavity. A method may further comprise delivering ultrasonic energy through the core cavity. The tissue resection device may be configured for the delivery of radiofrequency energy. The tissue resection device may be configured for mechanical transection. The tissue resection device may comprise mechanical compression and the delivery of radiofrequency energy. A method may further comprise amputating the core of tissue from the target tissue site. As an example, the means for amputation of the core of tissue may comprise mechanical transection. As a further example, the means for amputation of the core of tissue may comprise the delivery of radiofrequency energy. The means for amputation of the core of tissue may comprise mechanical compression and the delivery of radiofrequency energy. The means for amputation of the core of tissue may comprise transection with an energized wire. Other devices may be used.

A method for removing a core of tissue may comprise introducing a tissue resection device to a target tissue site, causing the tissue resection device to resect a core of tissue from the target tissue site, and removing the core of tissue from the body. A method may further comprise creating a core cavity at the target tissue site. A method may further comprise inserting a sleeve into the core cavity. A method may further comprise delivering radiofrequency energy through the core cavity. A method may further comprise delivering chemotherapy through the core cavity. A method may further comprise delivering microwave radiation through the core cavity. A method may further comprise delivering thermal energy through the core cavity. A method may further comprise delivering ultrasonic energy through the core cavity. The tissue resection device may be configured for the delivery of radiofrequency energy. The tissue resection device may be configured for mechanical transection. The tissue resection device may be configured for mechanical compression and the delivery of radiofrequency energy. A method may further comprise amputating the core of tissue from the target tissue site. The means for amputation of the core of tissue may comprise mechanical transection. The means for amputation of the core of tissue may comprise the delivery of radiofrequency energy. The means for amputation of the core of tissue may comprise mechanical compression and the delivery of radiofrequency energy. The means for amputation of the core of tissue may comprise transection with an energized wire.

A method for removing a core of tissue may comprise introducing a tissue resection device to a target tissue site. The tissue resection device may comprise one or more of: a first clamping element comprising a helical coil and a first electrode, or a second clamping element comprising a second electrode. Where a second clamping element is included, the second clamping element may be positioned to oppose at least a portion of the first clamping element. The method may further comprise causing the tissue resection device to resect a core of tissue from the target tissue site and removing the core of tissue from the body. A method may further comprise creating a core cavity at the target tissue site. A method may further comprise inserting a sleeve into the core cavity. A method may further comprise delivering radiofrequency energy through the core cavity. A method may further comprise delivering chemotherapy through the core cavity. A method may further comprise delivering microwave radiation through the core cavity. A method may further comprise delivering thermal energy through the core cavity. A method may further comprise delivering ultrasonic energy through the core cavity. The tissue resection device may be configured for resecting the core of tissue comprises the delivery of radiofrequency energy. The tissue resection device may be configured for resecting the core of tissue comprises mechanical transection. The tissue resection device may be configured for resecting the core of tissue comprises mechanical compression and the delivery of radiofrequency energy. A method may further comprise amputating the core of tissue from the target tissue site. The means for amputation of the core of tissue may comprise mechanical transection. The means for amputation of the core of tissue may comprise the delivery of radiofrequency energy. The means for amputation of the core of tissue may comprise mechanical compression and the delivery of radiofrequency energy. The means for amputation of the core of tissue may comprise transection with an energized wire.

A method for sealing biological fluid vessels may comprise piercing a target tissue site containing a least a portion of at least one target biological fluid vessel with a helical tissue sealing mechanism. The helical tissue sealing mechanism may comprise a helical piercing element and a clamping element. The method may comprise causing the helical tissue sealing mechanism to apply mechanical compression to at least one target biological fluid vessel and delivering energy to seal at least one target biological fluid vessel. The helical piercing element may comprise the clamping element. The mechanical compression may be applied between the helical piercing element and the clamping element. A method may further comprise a second clamping element. The mechanical compression may be applied between the first and second clamping elements. The delivered energy may comprise monopolar radiofrequency energy. The delivered energy may comprise bipolar radiofrequency energy. The delivered energy may comprise thermal energy. The delivered energy may comprise ultrasonic energy.

A method for sealing biological fluid vessels may comprise piercing a target tissue site with a helical piercing element, adjusting the pitch of the helical piercing element to apply mechanical compression to the target tissue, and delivering energy to seal at least one biological fluid vessel in the target tissue. The helical piercing element may comprise a plurality of tissue sealing electrodes. The delivered energy may comprise monopolar radiofrequency energy. The delivered energy may comprise bipolar radiofrequency energy. The delivered energy may comprise thermal energy. The delivered energy may comprise ultrasonic energy.

A tissue resection apparatus may comprise a first clamping element comprising a helical coil, a second clamping element, the second clamping element being positioned to oppose at least a portion of the first clamping element, a first and second electrode configured for the delivery of radiofrequency energy for sealing tissue, and a cutting element configured for the transection of at least a portion of the sealed tissue. A tissue resection device may further comprise: a first actuator operable to actuate the first or second clamping element to apply mechanical compression to tissue and a second actuator operable to actuate the cutting element to transect tissue. The helical coil may include first and second contiguous coil segments. The first coil segment may comprise a generally planar open ring. The first coil segment may be helical and may have a pitch of zero. The second coil segment may be helical and may have a non-zero pitch. The second coil segment may have a variable pitch. The first coil segment may be helical and may have a first pitch and the second coil segment may be helical and may have a second pitch, and at least one of the first and second pitches may be variable. The first electrode may be comprised of at least a portion of the first clamping element. The second electrode may be comprised of at least a portion of the second clamping element. The helical coil may comprise a blunt tip. The first and second electrodes may comprise surface profiles that are matching or substantially matching. At least a portion of the cutting element may comprise a sharpened edge. The cutting element may comprise at least one electrode configured for the delivery of radiofrequency energy. The cutting element may comprise an ultrasonic blade. The tissue resection device may further comprise a second cutting element configured for the amputation the core of tissue from the target tissue site. At least a portion of the second cutting element may comprise a sharpened edge. The second cutting element may comprise at least one electrode configured for the delivery of radiofrequency energy. The second cutting element may comprise an energized wire. The second cutting element may comprises a suture. The tissue resection device may further comprise an actuator operable to actuate the second cutting element to transect tissue.

A tissue resection apparatus may comprise a first clamping element having a helical coil disposed on a distal end, a second clamping element, the second clamping element being positioned to oppose at least a portion of the first clamping element, a first and second electrode configured for the delivery of radiofrequency energy for sealing tissue, and a cutting element configured for the transection of at least a portion of the sealed tissue. The tissue resection device may further comprise a first actuator operable to actuate the first or second clamping element to apply mechanical compression to tissue and a second actuator operable to actuate the cutting element to transect tissue. The helical coil may comprise first and second contiguous coil segments. The first coil segment may comprise a generally planar open ring. The first coil segment may be helical and may have a pitch of zero. The second coil segment may be helical and may have a non-zero pitch. The second coil segment may have a variable pitch. The first coil segment may be helical and may have a first pitch and the second coil segment may be helical and may have a second pitch, and at least one of the first and second pitches may be variable. The first electrode may be comprised of at least a portion of the helical coil. The first electrode may be comprised of at least a portion of the first clamping element. The second electrode may be comprised of at least a portion of the second clamping element. The helical coil may comprise a blunt tip. The first and second electrodes may comprise surface profiles that are matching or substantially matching. At least a portion of the cutting element may comprise a sharpened edge. The cutting element may comprise at least one electrode configured for the delivery of radiofrequency energy. The cutting element may comprise an ultrasonic blade. The tissue resection device may further comprise a second cutting element configured for the amputation the core of tissue from the target tissue site. At least a portion of the second cutting element may comprise a sharpened edge. The second cutting element may comprise at least one electrode configured for the delivery of radiofrequency energy. The second cutting element may comprise an energized wire. The second cutting element may comprise a suture. The tissue resection device may further comprise an actuator operable to actuate the second cutting element to transect tissue.

A tissue resection apparatus may comprise a first clamping element comprising a helical coil and a first electrode, and a second clamping element comprising a second electrode, the second clamping element being positioned to oppose at least a portion of the first clamping element. The first and second clamping elements may be configured for: (a) the delivery of radiofrequency energy for sealing tissue, and (b) the application of mechanical compression for the transection of tissue. The tissue resection device may further comprise a first actuator operable to actuate the first or second clamping element to apply mechanical compression to tissue and a second actuator operable to actuate the cutting element to transect tissue. The helical coil may comprise first and second contiguous coil segments. The first coil segment may comprise a generally planar open ring. The first coil segment may be helical and may have a pitch of zero. The second coil segment may be helical and may have a non-zero pitch. The second coil segment may have a variable pitch. The first coil segment may be helical and may have a first pitch and the second coil segment may be helical and may have a second pitch, and at least one of the first and second pitches may be variable. The first electrode may be comprised by at least a portion of the helical coil. The first electrode may be comprised of at least a portion of the first clamping element. The second electrode may be comprised of at least a portion of the second clamping element. The helical coil may comprise a blunt tip. The first and second electrodes may comprise surface profiles that are matching or substantially matching. At least a portion of the cutting element may comprise a sharpened edge. The cutting element may comprise at least one electrode configured for the delivery of radiofrequency energy. The cutting element may comprise an ultrasonic blade. The tissue resection device may further comprise a second cutting element configured for the amputation the core of tissue from the target tissue site. At least a portion of the second cutting element may comprise a sharpened edge. The second cutting element may comprise at least one electrode configured for the delivery of radiofrequency energy. The second cutting element may comprise an energized wire. The second cutting element may comprise a suture. The tissue resection device may further comprise an actuator operable to actuate the second cutting element to transect tissue.

A surgical instrument system for the resection of tissue may comprise an end effector operable to cut and seal tissue, wherein the end effector and a generator configured to provide power to the end effector having the first and second electrodes for sealing tissue. The end effector may comprise a first clamping element comprising a helical coil, a second clamping element, the second clamping element being positioned to oppose at least a portion of the first clamping element, a first and second electrode configured for the delivery of radiofrequency energy for sealing tissue, and a cutting element configured for the transection of at least a portion of the sealed tissue. The surgical instrument system may further comprise a controller in communication with the generator, wherein the controller is configured to control the generator to provide radiofrequency energy sufficient to seal tissue to the first and second electrodes of the end effector, based on at least one sensed operating condition of the end effector. The controller may be configured to sense the presence of tissue at the end effector. The controller may be configured to sense the presence of tissue at the end effector based on a measured impedance level associated with the first and second electrodes. The controller may be configured to sense an amount of force applied to at least one of the first or second clamping elements to detect the presence of tissue at the end effector. The controller may be configured to sense the position of the cutting element relative to at least one of the first or second clamping elements. The controller may be configured to control the generator to provide radiofrequency energy at the end effector when the second actuator is actuated and no tissue is sensed at the end effector. The controller may be configured to control the generator to provide a continuous amount of radiofrequency energy. The controller may be configured to control the generator to automatically provide an increase or decrease in the amount of radiofrequency energy. The system may further comprise a first actuator operable to actuate the first or second clamping element to apply mechanical compression to tissue, and a second actuator operable to actuate the cutting element to transect tissue. The helical coil may comprise first and second contiguous coil segments, the first coil segment including the first electrode. The first coil segment may comprise a generally planar open ring. The first coil segment may be helical and may have a pitch of zero. The second coil segment may be helical and may have a non-zero pitch. The second coil segment may have a variable pitch. The first coil segment may be helical and may have a first pitch and the second coil segment may be helical and may have a second pitch, and at least one of the first and second pitches may be variable. The first electrode may be comprised of at least a portion of the helical coil. The first electrode may be comprised of at least a portion of the first clamping element. The second electrode may be comprised of at least a portion of the second clamping element. The helical coil may comprise a blunt tip. The first and second electrodes may comprise surface profiles that are matching or substantially matching. At least a portion of the cutting element may comprise a sharpened edge. The cutting element may comprise at least one electrode configured for the delivery of radiofrequency energy. The cutting element may comprise an ultrasonic blade. The tissue resection device may further comprise a second cutting element configured for the amputation the core of tissue from the target tissue site. At least a portion of the second cutting element may comprise a sharpened edge. The second cutting element may comprise at least one electrode configured for the delivery of radiofrequency energy. The second cutting element may comprise an energized wire. The second cutting element may comprise a suture. The tissue resection device may further comprise an actuator operable to actuate the second cutting element to transect tissue.

A tissue resection apparatus may comprise a first clamping element comprising a helical coil, a second clamping element, the second clamping element being positioned to oppose at least a portion of the first clamping element, a first and second electrode configured for the delivery of radiofrequency energy for sealing tissue, a first cutting element configured for the transection of at least a portion of the sealed tissue, a first and second ligating element, and a second cutting element positioned between said first and second ligating elements. The tissue resection device may further comprise a first actuator operable to actuate the first or second clamping element to apply mechanical compression to tissue, and a second actuator operable to actuate the cutting element to transect tissue. The helical coil may comprise first and second contiguous coil segments. The first coil segment may comprise a generally planar open ring. The first coil segment may be helical and may have a pitch of zero. The second coil segment may be helical and may have a non-zero pitch. The second coil segment may have a variable pitch. The first coil segment may be helical and may have a first pitch and the second coil segment may be helical and may have a second pitch, and at least one of the first and second pitches may be variable. The first electrode may be comprised of at least a portion of the helical coil. The first electrode may be comprised of at least a portion of the first clamping element. The second electrode may be comprised of at least a portion of the second clamping element. The helical coil may comprise a blunt tip. The first and second electrodes may comprise surface profiles that are matching or substantially matching. At least a portion of the cutting element may comprise a sharpened edge. The cutting element may comprise at least one electrode configured for the delivery of radiofrequency energy. The cutting element may comprise an ultrasonic blade. The tissue resection device may further comprise a second cutting element configured for the amputation the core of tissue from the target tissue site. At least a portion of the second cutting element may comprise a sharpened edge. The second cutting element may comprise at least one electrode configured for the delivery of radiofrequency energy. The second cutting element may comprise an energized wire. The second cutting element may comprise a suture. The tissue resection device may further comprise an actuator operable to actuate the second cutting element to transect tissue.

A tissue sealing mechanism may comprise a helical coil with a generally obround cross section and a tapered point disposed at a distal end, a first and second helical tissue sealing surface, wherein the first and second helical tissue sealing surfaces are provided by the parallel planar surfaces of the helical coil, a first electrode disposed on the first helical tissue sealing surface, and a second electrode disposed on the second helical tissue sealing surface, wherein the first and second electrodes are configured to apply bipolar radiofrequency energy for sealing tissue. The helical coil may comprise first and second contiguous coil segments. The helical coil may comprise a blunt tip. The first and second electrodes may have surface profiles that are substantially matching. The first and second helical tissue sealing surfaces may further comprise a plurality of electrodes configured for the delivery of bipolar radiofrequency energy.

FIGS. 11-17 shown examples devices that may be used to effect a coring process, as described herein. For example, a resection device of the present invention may comprise an energy-based arrangement capable of penetrating tissue towards a target lesion. In one embodiment depicted in FIG. 11, tissue resection device 1100 includes an outer tube 1105 is provided having a distal edge profile and having an inner diameter IDouter. A coil 1110 is attached to an outer tube 1105 where the coil turns are spaced from and opposed to a distal end of the outer tube 1105. The coil 1110 preferably has a slightly blunted tip 1115 to minimize the possibility that it will penetrate through a blood vessel while being sufficiently sharp to penetrate tissue such as pleura and parenchyma. In some embodiments, the coil 1110 may take the form of a helix having a constant or variable pitch. The coil 1110 may also have a variable cross-sectional geometry. An electrode 1130 may be disposed on a surface or embedded within the coil 1110.

Figure 11:
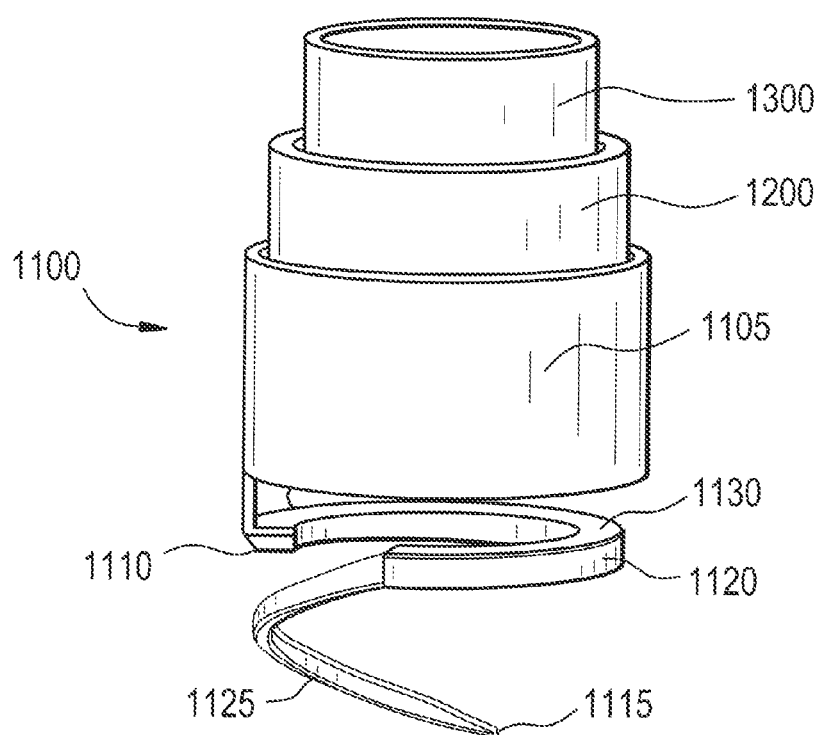
FIG. 11 depicts a tissue resection device in accordance with an embodiment of the present disclosure.

In some embodiments, as illustrated in FIG. 11, the coil 1110 may include a plurality of contiguous coil segments, e.g., coil segments 1120 and 1125. The coil segment 1120 may comprises a helical member having a pitch of zero, e.g., a generally planar open ring structure, having an inner diameter IDcoil and an outer diameter ODcoil. The coil segment 1125 may comprise a helical structure of constant or variable pitch and constant or variable cross-sectional geometry. In this embodiment, the electrode 1130 may be disposed on a surface of or embedded in the coil segment 1120.

Figure 12:
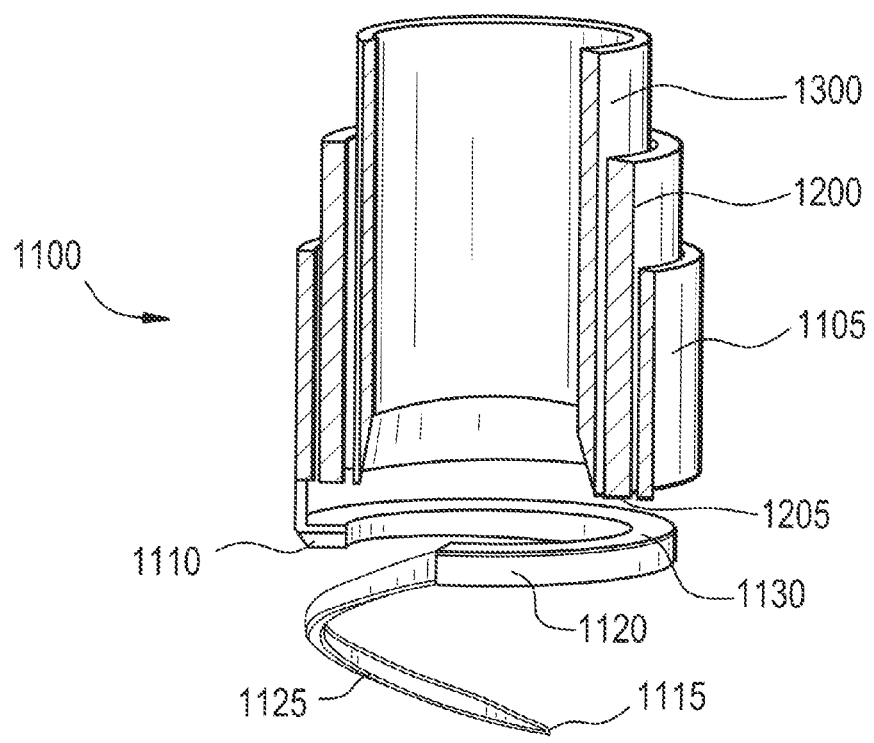
FIG. 12 illustrates a sectional view of the tissue resection device of FIG. 1.

A central tube 1200 may be provided having a distal end with an edge profile comprising one or more surface segments and having an outer diameter ODcentral and an inner diameter IDcentral. As illustrated in FIG. 12, an electrode 1205 is disposed on or embedded within at least one of the surface segments. The central tube 1200 is slidably disposed within the outer tube 1105 and positioned such that the electrode 1205 opposes and overlaps at least a portion of electrode 1130. The space between electrode 1205 and electrode 1130 may be referred to as the tissue clamping zone. In keeping with an aspect of the present disclosure, ODcentral>IDcoil and ODcoil>IDcentral. In some embodiments, ODcentral is about equal to ODcoil. Accordingly, the central tube 1200 may be advanced through the tissue clamping zone towards coil 1110 such that electrode 1205 abuts electrode 1130.

A cutting tube 1300 may be slidably disposed within the central tube 1200. The distal end of the cutting tube 1300 is provided with a knife edge to facilitate tissue cutting.

To enable tissue resection, the resection device 1100 may be inserted into tissue and the outer tube 1105 may be advanced a predetermined distance towards a target. The coil segment 1125 may allow the device to penetrate the tissue in a manner similar to a cork screw. As the coil segment 1125 penetrates tissue, any vessel in its path may either be moved to planar coil segment 1120 or pushed away from the coil 1100 for subsequent turns. A coil tip 1115 may be made blunt enough to minimize chances that it will penetrate through a blood vessel, while still sharp enough to penetrate certain tissue, such as the lung pleura and parenchyma. The central tube 1200 may then be advanced a predetermined distance towards the target. Any vessels that are disposed in the tissue clamping zone will be clamped between electrode 1130 and electrode 1205. The vessels may then be sealed by the application of bipolar energy to electrode 1130 and electrode 1205. Once blood vessels are sealed, the cutting tube 1300 may be advanced to core the tissue to the depth that the outer tube 1105 has reached. The sealing and cutting process can be repeated to create a core of desired size.

Figure 13:
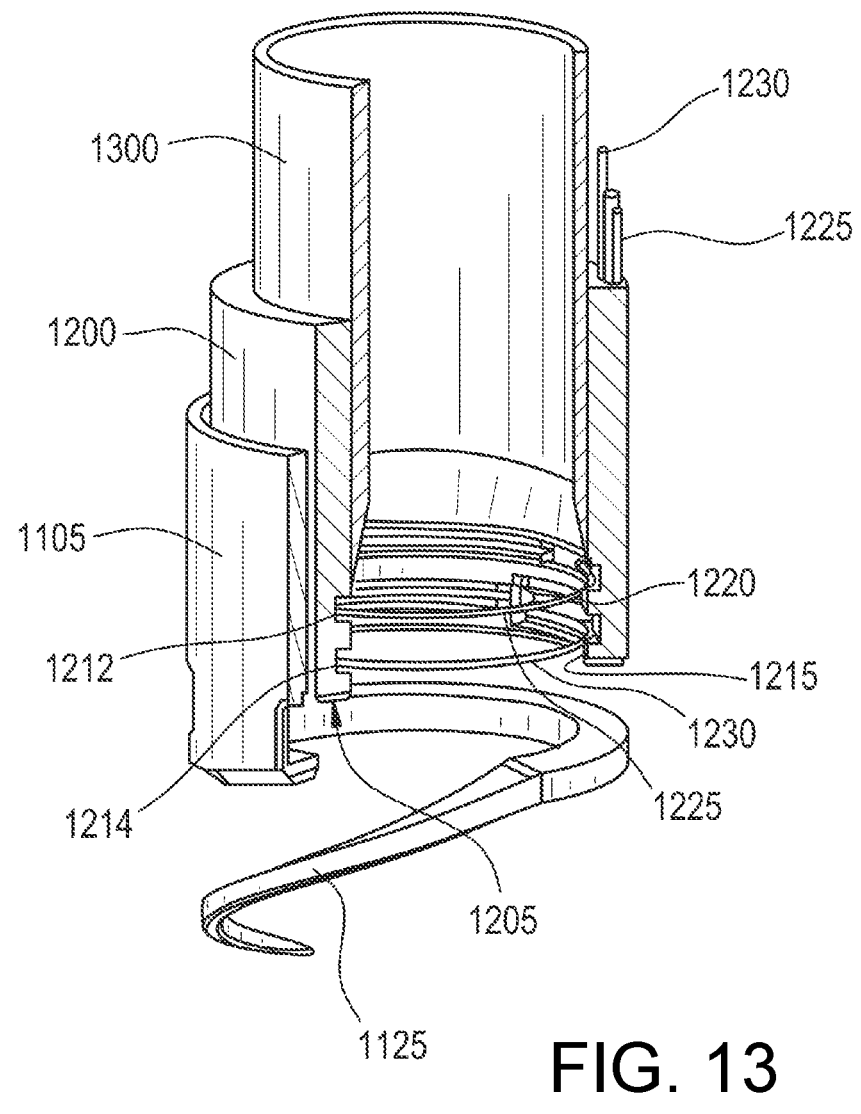
FIG. 13 shows a sectional view of a tissue resection device in accordance with an embodiment of the present disclosure.
Figure 14:
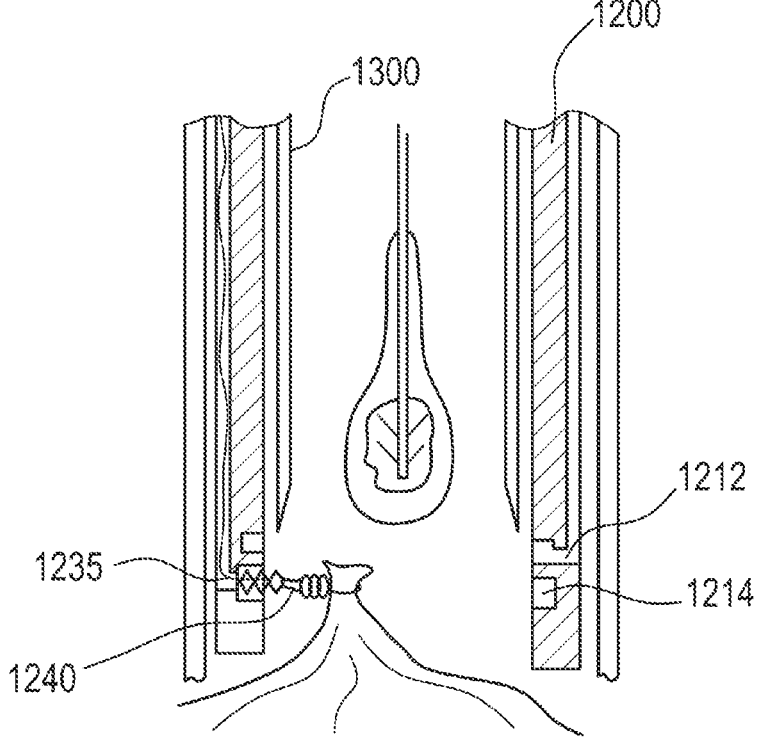
FIG. 14 depicts a sectional view of a tissue resection device in accordance with an embodiment of the present disclosure.

In keeping with an aspect of the present disclosure, the resection device may be further configured to dissect a target lesion and seal tissue proximate the dissection point. To facilitate dissection and sealing, as illustrated in FIG. 13, the central tube 1200 is provided with a ligation snare 1230, first and second ligation electrodes 1215 and 1220, and an amputation snare 1225. As used herein, the word "snare" refers to a flexible line, e.g., a string or a wire. The inner wall surface of the central tube 1200 may include upper and lower circumferential grooved pathways 1212 and 1214 disposed proximate the distal end. The first and second ligation electrodes 1215 and 1220 may be disposed on the inner wall of central tube 1200 such that lower circumferential groove 1214 may be between them. The upper grooved pathway 1212 may be disposed axially above the ligation electrodes 1215 and 1220.

The ligation snare 1230 may be disposed in the lower circumferential groove 1214 and extends through the central tube 1200 and axially along the outer wall surface to a snare activation mechanism (not shown). The amputation snare 1225 may be disposed in the upper circumferential groove 1212 and extends through the central tube 1200 and axially along the outer wall surface to a snare activation mechanism (not shown). The outer surface of the central tube 1200 may be provided with a plurality of axially extending grooved pathways which receive the amputation snare 1225 and the ligation snare 1230 and are in communication with the upper and lower circumferential grooved pathways 1212 and 1214. In addition, electrode leads for the ligation electrodes 1215 and 1220 may extend to an energy source via the axially extending grooved pathways.

In operation, the resection device of this embodiment may detach and seal the tissue core. The cutting tube 1300 may be retracted to expose the ligation snare 1230 which is preferably made of flexible line, e.g., suture. The ligation snare 1230 may be engaged to snag tissue and pull tissue against the inner wall surface between the first and second ligation electrodes 1215 and 1220. Bipolar energy may then be applied to the first and second electrodes 1215 and 1220 to seal, i.e., cauterize, the tissue. Once sealed, the cutting tube 1300 may be further retracted to expose the amputation snare 1225 which may then be activated to sever the tissue core upstream from the point where the tissue was sealed (ligation point). In some embodiments, the amputation snare 1225 has a smaller diameter than that of ligation snare 1230. The smaller diameter facilitates tissue slicing. Accordingly, the resection device 1100 according to this embodiment may both create a tissue core and disengage the core from surrounding tissue.

In an alternative embodiment, the resection device of the present disclosure may be provided with a single snare disposed between ligation electrodes which both ligates and cuts tissue. In this embodiment, the single snare may first pull tissue against the inner wall surface of the central tube 1200 between the ligation electrodes 1215 and 1220. Bipolar energy may then applied to the first and second electrodes 1215 and 1220 to seal, i.e., cauterize, the tissue. Once sealed, the snare may further pulled to sever the tissue core.

In yet another embodiment, cutting and sealing may be performed without employing electrodes. In this embodiment, the ligation snare 1230 may include a set of knots 1235 and 1240 which tighten under load, shown, for example, in FIG. 14. Ligation is performed by retracting the cutting tube 1300 to expose the ligation snare 1230 and activating the ligation snare 1230, which lassos tissue as ligation knot tightens. Once the tissue is lassoed, the cutting tube 1300 may be further retracted to expose the amputation snare 1225 which may then be activated to sever the tissue core upstream from the point where the point where the tissue was lassoed.

The present disclosure also contemplates a method and system for using the resection device to remove tissue lesions, for example, lung lesions. The method generally comprises anchoring the lesion targeted for removal, creating a channel in the tissue leading to the target lesion, creating a tissue core which includes the anchored lesion, ligating the tissue core and sealing the surrounding tissue, and removing the tissue core including the target lesion from the channel.

Anchoring may be performed by, any suitable structure for securing the device to the lung. Once the lesion is anchored, a channel may be created to facilitate insertion of the resection device 1100. The channel may be created by making an incision in the lung area and inserting a tissue dilator and port into the incision. A tissue core which includes the anchored lesion may be created. In keeping with the present disclosure, the resection device 1100 may be used to create the tissue core, to ligate the tissue core and to seal the tissue core and sever it from the surrounding tissue as described hereinabove. The tissue core may then be removed from the channel. As an example, a cavity port may be inserted in the channel to facilitate subsequent treatment of the target lesion site through chemotherapy and/or energy-based tumor extirpation such as radiation. As a further example, a cavity port may be disposed on the perimeter of the tissue resection apparatus. When the apparatus is removed from the tissue site, the cavity port may remain in place or may be removed.

Figure 15:
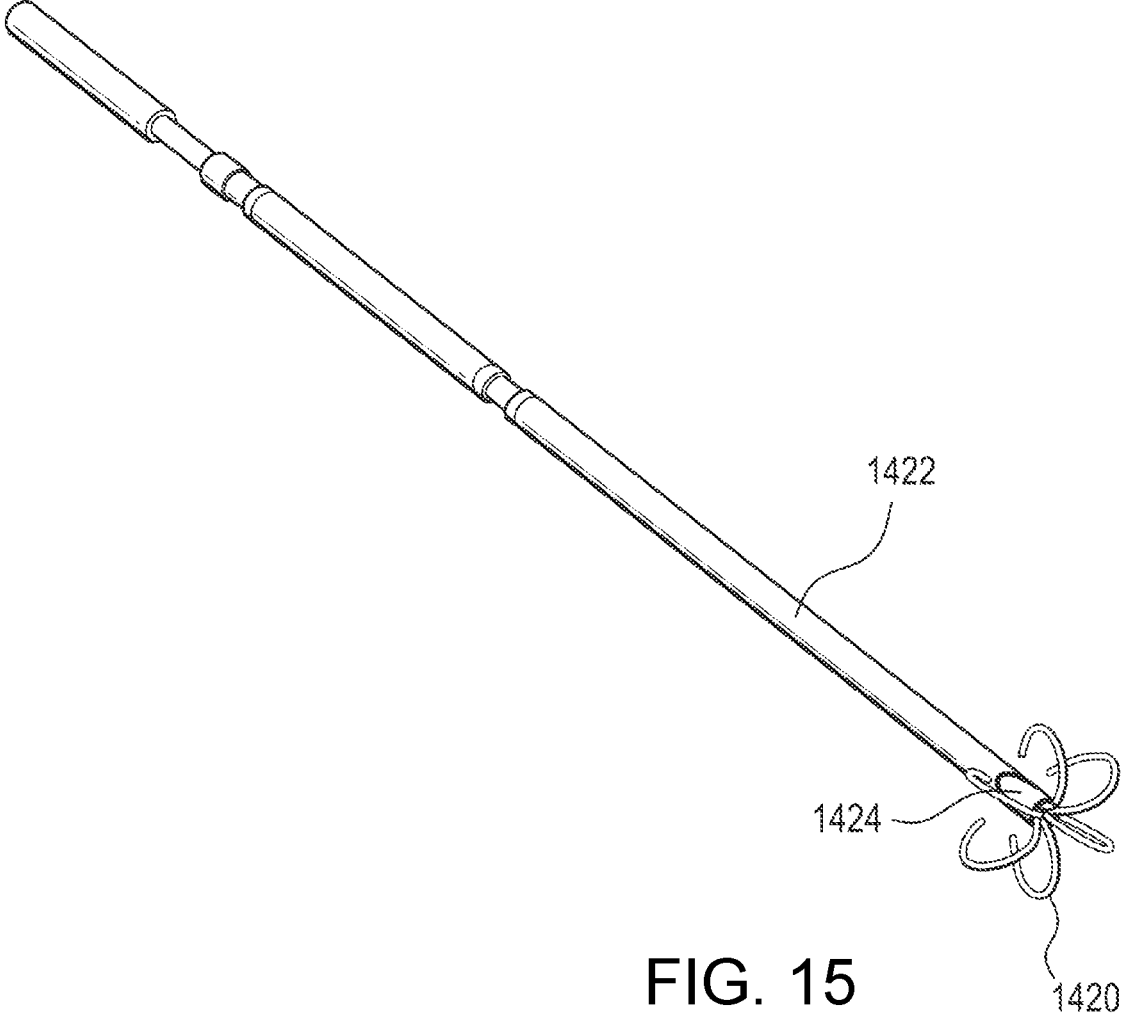
FIG. 15 illustrates an exemplary anchor that may be employed in a lesion removal method in accordance with an embodiment of the present disclosure.

The anchor depicted in FIG. 15 may be suitable for use in performing the method for removing tissue lesions described herein. The anchor may comprise an outer tube 1422 having a sufficiently sharp edge to pierce the chest cavity tissue and lung without causing excess damage and an inner tube 1424 disposed within the outer tube 1422. One or more tines or fingers 1426 formed or preformed from shape memory material, e.g., Nitinol, may be attached to the end of inner tube 1424. The outer tube 1422 may be retractably disposed over the inner tube 1424 such that when the outer tube 1422 may be retracted, the tines 1426 assume their preform shape as shown. In keeping with the present disclosure, the outer tube 1422 may be retracted after it has pierced the lung lesion thereby causing the tines 1426 to engage the lung lesion. Other suitable anchors may include coils and suction-based structures.

Figure 16:
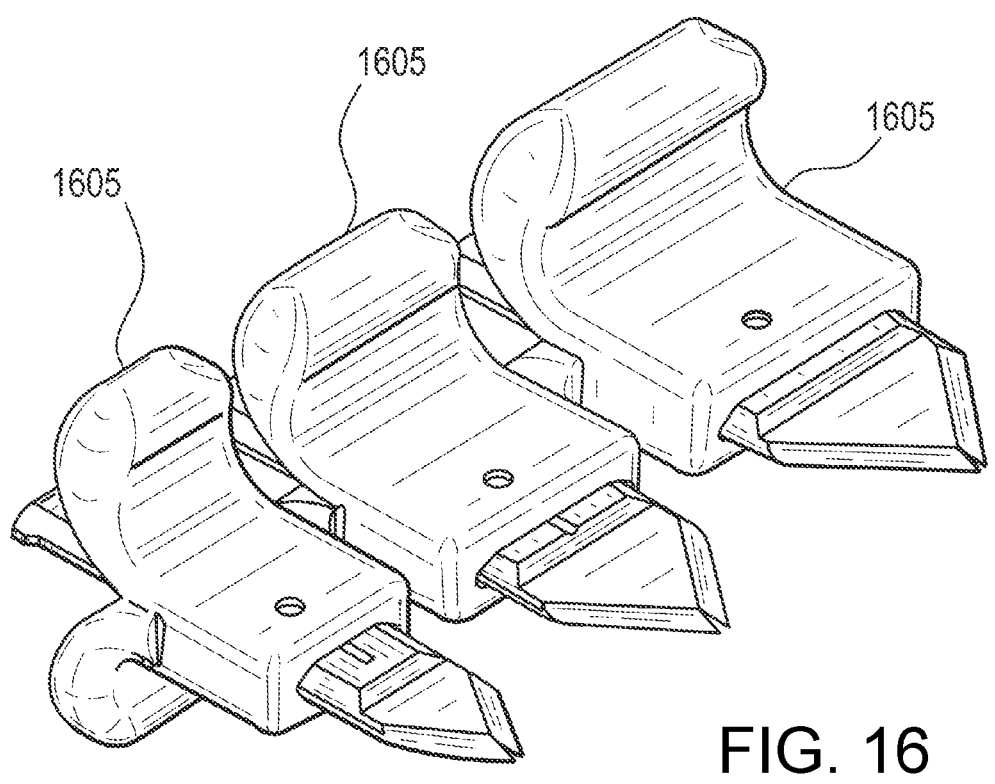
FIG. 16 shows a series of incision blades for use in a lesion removal method in accordance with an embodiment of the present disclosure.

The incision blades depicted in FIG. 16 are suitable for use in performing the method for removing tissue lesions described herein. Once the anchor 1400 is set, it may be preferable to create a small cut or incision to facilitate insertion of chest wall tissue dilator. Incision blades 1605 may be used to make a wider cut. The incision blades 1605 may successive. The incision blades 1605 may include a central aperture which may allow them to be coaxially advanced along the anchor needle 1405 to create a wider cut in the chest wall, with each successive blade being larger than the previous blade, thereby increasing the width of the incision.

Figure 17:
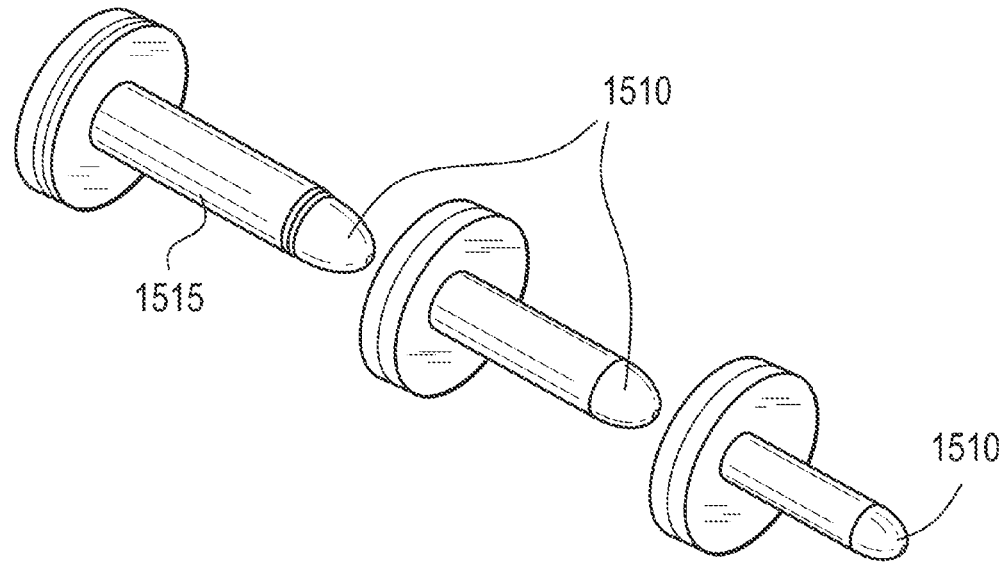
FIG. 17 displays tissue dilators suitable for use in a lesion removal method in accordance with an embodiment of the present disclosure.

The tissue dilator depicted in FIG. 17 may be suitable for use in performing the method for removing tissue lesions described herein. The tissue dilator may comprise any suitable device for creating a channel in organic tissue. In one exemplary embodiment, the tissue dilator assembly includes a single cylindrical rod with a rounded end 1510 or a cylindrical rod with rounded end and a rigid sleeve arrangement 1515. Successive tissue dilators may be coaxially advanced along the anchor needle to create tissue tract or channel in the chest wall, with each successive dilator being larger than the previous dilator, thereby increasing the diameter of the channel. Once a final dilator with rigid sleeve is deployed, the inner rod 1505 may be removed, leaving the rigid sleeve in the intercostal space between ribs to create direct passage to the lung pleura.

Any tissue resection device capable of penetrating lung tissue and creating a tissue core including a target lesion may be suitable for use in performing the method for removing tissue lesions described herein. The tissue resection device 1100 described hereinbefore is preferred.

Once the tissue resection device 1100 is removed, a small channel in the lung may exist where the target lesion was removed. This channel may be utilized to introduce an energy-based ablation device and/or localized chemotherapy depending on the results of the tissue diagnosis. Accordingly, the method and system of the present disclosure may not only be utilized to ensure an effective biopsy is performed but also complete removal of the lesion with minimal healthy lung tissue removal is accomplished.

Figure 18:
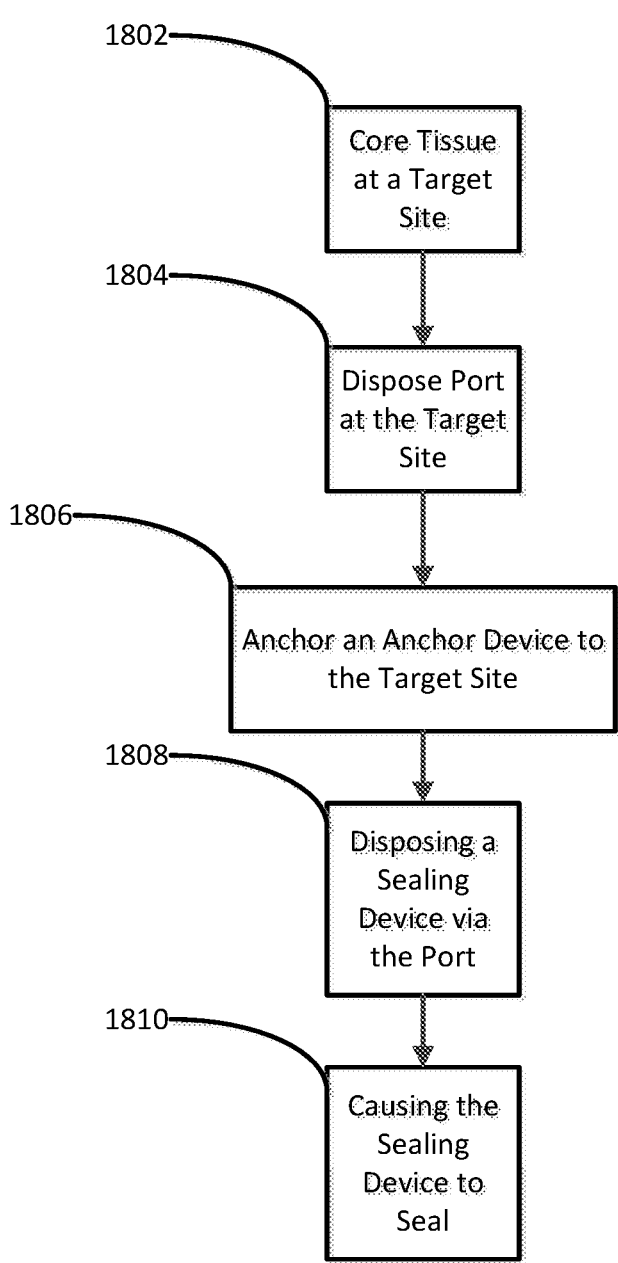
FIG. 18 shows a flow diagram of an example method for coring and for sealing tissue.

FIG. 18 shows a flow diagram of an example method. At 1802, tissue at a target site may be cored such that a tissue core is removed from the target site thereby creating a core cavity at the target site. Coring tissue at a target site may comprise transecting and sealing tissue. Coring tissue at a target site may comprise disposing a tissue coring apparatus adjacent to a target tissue site. The tissue coring apparatus may comprise a first clamping element comprising a helical coil, a second clamping element, the second clamping element being positioned to oppose at least a portion of the first clamping element, a first and second electrode configured for the delivery of radiofrequency energy for sealing tissue, and/or a cutting element configured for the transection of at least a portion of the sealed tissue. Other apparatus may be used.

At 1804, a port may be disposed to provide access to a target site. A port (e.g., chest port 102 (FIG. 1)) may be disposed to provide access to a target site. A user may dispose a port to provide access to a target site. The target site may comprise biological tissue. The target site may comprise tissue of a lung. The target site may comprise a cored tissue. The target site may comprise a punctured tissue. The target site may comprise at least a portion of a lung.

At 1806, an anchor device may be anchored to a surface at the target site. As an example, a user may anchor the anchor device, via the port, to a surface at the target site.

At 1808, a sealing device may be disposed adjacent the target site, for example via the port. The sealing device may comprise an inflatable balloon. The sealing device may comprise an inflatable balloon catheter. The lung may be caused to collapse prior to disposing the sealing device adjacent the target site. The lung may be allowed to ventilate while the sealing device is sealing the target site.

At 1810, the sealing device may be caused to seal the target site. Causing the sealing device to seal the target site may comprise causing at least a portion of the sealing device to abut a portion of the target site.

The present disclosure comprises at least the following aspects:

Aspect 1. A method for sealing tissue at a target site, the method comprising: disposing a sealing device in a cavity at a target site of tissue, wherein the sealing device comprises an inflatable balloon; causing the balloon to inflate using a fluid such that at least a portion of the inflated balloon abuts a wall of the cavity to seal at least a portion of the cavity; and spacing the sealing device from the target site.

Aspect 2. The method of aspect 1, wherein the target site comprises tissue of a lung.

Aspect 3. The method of any one of aspects 1-2, wherein the fluid has a temperature sufficient to ablate at least a portion of the wall of the cavity.

Aspect 4. The method of any one of aspects 1-3, wherein the cavity comprises a cored tissue having a measurable radius and the balloon is inflated based on the radius.

Aspect 5. The method of any one of aspects 1-4, wherein the target site comprises at least a portion of a lung and further comprising causing the lung to collapse prior to disposing the sealing device in the cavity.

Aspect 6. The method of any one of aspects 1-5, wherein the target site comprises at least a portion of a lung and further comprising allowing the lung to ventilate while the sealing device is sealing the target site.

Aspect 7. The method of any one of aspects 1-6, wherein a bio-adhesive is disposed on a surface of the balloon such that the bio-adhesive contacts the wall of the cavity when the balloon is inflated.

Aspect 8. The method of any one of aspects 1-7, wherein the balloon is configured to delivery RF energy to at least a portion of the wall of the cavity.

Aspect 9. The method of any one of aspects 1-8, further comprising deflating the balloon for removal from the cavity.

Aspect 10. A method for sealing tissue at a target site, the method comprising: disposing a cavity sheath adjacent a tissue cavity to minimize collapse of the tissue cavity; disposing a sealing device in the tissue cavity, wherein the sealing device comprises an inflatable balloon; removing the cavity sheath from the tissue cavity such that the inflatable balloon remains disposed in the tissue cavity; and causing the balloon to inflate using a fluid such that at least a portion of the inflated balloon abuts a wall of the tissue cavity to seal at least a portion of the tissue cavity.

Aspect 11. The method of aspect 10, wherein the tissue cavity is formed in a lung.

Aspect 12. The method of any one of aspects 10-11, wherein the tissue cavity comprises a cored tissue.

Aspect 13. The method of any one of aspects 10-12, wherein the fluid has a temperature sufficient to ablate at least a portion of the wall of the tissue cavity.

Aspect 14. The method of any one of aspects 10-13, wherein the tissue cavity comprises a cored tissue having a measurable radius and the balloon is inflated based on the radius.

Aspect 15. The method of any one of aspects 10-14, wherein the tissue cavity is disposed in a lung and further comprising causing the lung to collapse prior to disposing the sealing device in the tissue cavity.

Aspect 16. The method of any one of aspects 10-15, wherein the tissue cavity is disposed in a lung and further comprising allowing the lung to ventilate while the sealing device is sealing the tissue cavity.

Aspect 17. The method of any one of aspects 10-16, further comprising deflating the balloon for removal from the tissue cavity.

Aspect 18. The method of any one of aspects 10-17, wherein a bio-adhesive is disposed on a surface of the balloon such that the bio-adhesive contacts the wall of the cavity when the balloon is inflated.

Aspect 19. The method of any one of aspects 10-18, wherein the balloon is configured to delivery RF energy to at least a portion of the wall of the cavity.

Aspect 20. The method of any one of aspects 10-19, further comprising removing the sealing device from the tissue cavity.

Aspect 21. A sealing device for sealing a tissue cavity, the sealing device comprising: a balloon catheter configured to extend an inflatable balloon into a tissue cavity; and a source of fluid in fluid communication with the inflatable balloon and configured to fill the balloon with a fluid to inflate the balloon to a controlled radius.

Aspect 22. The sealing device of aspect 21, wherein the tissue cavity is formed in a lung.

Aspect 23. The sealing device of any one of aspects 21-22, wherein the tissue cavity comprises a cored tissue having a measurable radius and the balloon is inflated based on the measurable radius.

Aspect 24. The sealing device of any one of aspects 21-23, wherein the fluid has a temperature sufficient to ablate at least a portion of a wall of the tissue cavity.

Aspect 25. The sealing device of any one of aspects 21-24, wherein a bio-adhesive is disposed on a surface of the balloon such that the bio-adhesive contacts a wall of the cavity when the balloon is inflated.

Aspect 26. The sealing device of any one of aspects 21-25, wherein the balloon is configured to delivery RF energy to at least a portion of a wall of the cavity.

Although shown and described is what is believed to be the most practical and preferred embodiments, it is apparent that departures from specific designs and methods described and shown will suggest themselves to those skilled in the art and may be used without departing from the spirit and scope of the invention. For example, the systems, devices and methods described herein for removal of lesions from the lung. It will be appreciated by the skilled artisan that the devices and methods described herein may are not limited to the lung and could be used for tissue resection and lesion removal in other areas of the body. The present invention is not restricted to the particular constructions described and illustrated, but should be constructed to cohere with all modifications that may fall within the scope of the appended claims.

What is claimed is:

1. A method for sealing tissue at a target site, the method comprising:

anchoring a distal end of an anchor device to a portion of the target site;

coring tissue at the target site to remove a section of cored tissue thereby creating a cored cavity;

disposing, after removing the section of cored tissue, a sealing device across an opening of the cored cavity;

causing at least a portion of the sealing device to seal across the opening of the cored cavity;

delivering, after at least the portion of the cored cavity is sealed, a fill material to the target site, the fill material including autologous blood configured to clot after a predetermined period of time;

holding the sealing device in place, via the anchor device, for the predetermined period of time to allow the autologous blood to clot at the target site; and spacing, after the predetermined period of time, the sealing device from the target site while leaving the fill material at the target site.

2. The method of claim 1, wherein the target site comprises tissue of a lung.

3. The method of claim 1, wherein the sealing device includes an inflatable balloon, and causing the portion of the sealing device to seal across the opening of the cored cavity includes inflating the inflatable balloon using a fluid.

4. The method of claim 1, wherein the sealing device includes an inflatable balloon, and causing the portion of the sealing device to seal across the opening of the cored cavity includes inflating the inflatable balloon to at least a radius of the cored cavity.

5. The method of claim 1, wherein the target site comprises at least a portion of a lung, the method further comprising causing the lung to collapse prior to disposing the sealing device across the opening of the cored cavity.

6. The method of claim 1, wherein the target site comprises at least a portion of a lung, the method further comprising allowing the lung to ventilate while the sealing device is sealing the opening of the cored cavity.

7. The method of claim 1, wherein a bio-adhesive is disposed on a surface of the sealing device such that the bio-adhesive contacts a wall of the cored cavity when the sealing device is caused to seal across the opening of the cored cavity.

8. The method of claim 1, wherein the sealing device is configured to deliver radiofrequency (RF) energy to at least a portion of a wall of the cored cavity.

9. The method of claim 1, wherein the sealing device includes an inflatable balloon, and causing the portion of the sealing device to seal across the opening of the cored cavity includes inflating the inflatable balloon, the method further comprising:

deflating the inflatable balloon for removal from the cored cavity.

10. A method for sealing tissue at a target site, the method comprising:

disposing a port adjacent to tissue;

anchoring a distal end of an anchor device to a portion of the target site;

removing, using a tissue resection device, a section of cored tissue to create a cored tissue cavity;

disposing, after removing the section of cored tissue, a sealing device through the port and adjacent to the cored tissue cavity while remaining outside of the cored tissue cavity;

causing at least a portion of the sealing device to seal across an opening of the cored tissue cavity;

delivering, after causing the portion of the sealing device to seal across the opening of the cored tissue cavity, a fill material to the target site, the fill material including autologous blood configured to clot after a predetermined period of time; and holding the sealing device in place, via the anchor device, for the predetermined period of time to allow the autologous blood to clot at the target site.

11. The method of claim 10, wherein the cored tissue cavity is formed in a lung.

12. The method of claim 10, wherein the sealing device includes an inflatable balloon, and causing the portion of the sealing device to seal across the opening of the cored tissue cavity includes inflating the inflatable balloon using a fluid.

13. The method of claim 10, wherein the sealing device includes an inflatable balloon, and causing the portion of the sealing device to seal across the opening of the cored tissue cavity includes inflating the inflatable balloon to at least radius of the cored tissue cavity.

14. The method of claim 10, wherein the cored tissue cavity is disposed in a lung, the method further comprising causing the lung to collapse prior to disposing the sealing device adjacent to the cored tissue cavity.

15. The method of claim 10, wherein the cored tissue cavity is disposed in a lung, the method further comprising allowing the lung to ventilate while the sealing device is sealing across the opening of the cored tissue cavity.

16. The method of claim 10, wherein the sealing device includes an inflatable balloon, and causing the portion of the sealing device to seal across the opening of the cored tissue cavity includes inflating the inflatable balloon, the method further comprising:

deflating the inflatable balloon for removal from the cored tissue cavity.

17. The method of claim 10, further comprising removing the sealing device from the cored tissue cavity.

18. A method for sealing tissue at a target site, the method comprising:

anchoring a distal end of an anchor device to a portion of the target site;

coring, using a coring device including a pair of electrodes, a tissue at a target site to remove a section of cored tissue thereby creating a cored cavity;

disposing, after removing the coring device and the section of cored tissue, a sealing device adjacent to or within the cored cavity;

causing at least a portion of the sealing device to abut a portion of the cored cavity to seal at least the portion of the cored cavity to form a sealed cavity;

delivering, using a fill material delivery device, a fill material to the sealed cavity, the fill material including autologous blood configured to clot after a predetermined period of time; and holding the sealing device in place, via the anchor device, for the predetermined period of time to allow the autologous blood to clot at the target site.

19. The method of claim 18, wherein the target site comprises tissue of a lung.

20. The method of claim 18, wherein the sealing device includes an inflatable balloon, and causing the portion of the sealing device to seal at least the portion of the cored cavity includes inflating the inflatable balloon using a fluid.

21. The method of claim 18, wherein a bio-adhesive is disposed on a surface of the sealing device such that the bio-adhesive contacts a wall of the cored cavity when the sealing device is caused to abut the portion of the cored cavity.

22. The method of claim 18, wherein the sealing device is configured to deliver radiofrequency (RF) energy to at least a portion of a wall of the cored cavity.

23. The method of claim 18, wherein the sealing device includes an inflatable balloon, and causing the sealing device to seal at least the portion of the cored cavity includes inflating the inflatable balloon to at least a radius of the cored cavity.

24. The method of claim 18, wherein the target site comprises at least a portion of a lung, the method further comprising causing the lung to collapse prior to disposing the sealing device adjacent to the cored cavity.

25. The method of claim 18, wherein the target site comprises at least a portion of a lung, the method further comprising allowing the lung to ventilate while the sealing device is sealing at least the portion of the cored cavity.

26. The method of claim 18, wherein a bio-adhesive is disposed on a surface of the sealing device such that the bio-adhesive contacts a wall of the cored cavity when the sealing device is caused to seal at least the portion of the cored cavity.

27. The method of claim 10, wherein the sealing device is configured to deliver radiofrequency (RF) energy to at least a portion of a wall of the cored tissue cavity.

\* \* \* \* \*